US012674147B2

(12) United States Patent
An et al.

(10) Patent No.: US 12,674,147 B2
(45) Date of Patent: Jul. 7, 2026

(54) CHIMERIC DNA POLYMERASE AND APPLICATION THEREOF

(71) Applicant: BGI SHENZHEN, Shenzhen (CN)

(72) Inventors: Qun An, Shenzhen (CN); Miaomiao Guo, Shenzhen (CN); Feng Xi, Shenzhen (CN); Fei Guo, Shenzhen (CN); Yue Zheng, Shenzhen (CN); Yuliang Dong, Shenzhen (CN); Wenwei Zhang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 732 days.

(21) Appl. No.: 17/787,955

(22) PCT Filed: Dec. 23, 2019

(86) PCT No.: PCT/CN2019/127462
§ 371 (c)(1),
(2) Date: Jun. 22, 2022

(87) PCT Pub. No.: WO2021/127848
PCT Pub. Date: Jul. 1, 2021

(65) Prior Publication Data
US 2024/0200040 A1 Jun. 20, 2024

(51) Int. Cl.
*C12P 19/34* (2006.01)
*C12N 9/12* (2006.01)
*C12Q 1/48* (2006.01)

(52) U.S. Cl.
CPC ............ *C12N 9/1252* (2013.01); *C12P 19/34* (2013.01); *C12Q 1/485* (2013.01); *C12Y 207/07007* (2013.01)

(58) Field of Classification Search
CPC ....... C12N 9/1252; C12P 19/34; C12Q 1/485; C12Y 207/07007
See application file for complete search history.

(56) References Cited

U.S. PATENT DOCUMENTS 9,023,633 B2 * 5/2015 Faurholm ............... C12P 19/34
435/194

FOREIGN PATENT DOCUMENTS

| | | |
|---|---|---|
| CN | 102257136 A | 11/2011 |
| CN | 108064278 A | 5/2018 |
| CN | 109628424 A | 4/2019 |
| EP | 1925669 B1 | 12/2010 |
| WO | 2004058942 A2 | 7/2004 |

OTHER PUBLICATIONS

"Alignment," downloaded Apr. 4, 2025 from <https://abss.uspto.gov/abss4examiners/> (Year: 2025).*
"KOD Domain Alignment" downloaded from <https://abss.uspto.gov/abss4examiners/> on Aug. 28, 2025 as a PDF (Year: 2025).*
"Pfu Domain Alignment" downloaded from <https://abss.uspto.gov/abss4examiners/> on Aug. 28, 2025 as a PDF (Year: 2025).*
"Pab Domain Alignment" downloaded from <https://abss.uspto.gov/abss4examiners/> on Aug. 28, 2025 as a PDF (Year: 2025).*
Marta Spibida et al., "Modified DNA polymerases for PCR trouble-shooting", J Appl Genetics, vol. 58, Oct. 28, 2016, pp. 133-142, DOI: 10.1007/s13353-016-0371-4.
Xuan Chen et al., "Screening and prenatal genetic diagnosis of Fragile X syndrome using Pfu DNA polymerase", Chinese Journal of Birth Health & Heredity, vol. 12, No. 3, Dec. 31, 2004, pp. 25, 22.

* cited by examiner

*Primary Examiner* — Suzanne M Noakes
*Assistant Examiner* — Ciara A McKnight
(74) *Attorney, Agent, or Firm* — BOND, SCHOENECK & KING, PLLC; George R. McGuire

(57) ABSTRACT

A chimeric DNA polymerase includes: a first fragment having at least 80% homology to at least part of an N-end domain of KOD DNA polymerase; a second fragment having at least 80% homology to at least part of an exonucleolytic domain of Pab DNA polymerase; a third fragment having at least 80% homology to at least part of the N-end domain of KOD DNA polymerase; a fourth fragment having at least 80% homology to at least part of a palm domain of Pfu DNA polymerase; a fifth fragment having at least 80% homology to at least part of a finger domain of Pab DNA polymerase; a sixth fragment having at least 80% homology to at least part of the palm domain of Pfu DNA polymerase; and a seventh fragment having at least 80% homology to at least part of a thumb domain of KOD DNA polymerase.

13 Claims, 3 Drawing Sheets
Specification includes a Sequence Listing.

SEQUENCE LISTING

```
<160> NUMBER OF SEQ ID NOS: 16

<210> SEQ ID NO 1
<211> LENGTH: 775
<212> TYPE: PRT
<213> ORGANISM: Artificial Sequence
<220> FEATURE:
<223> OTHER INFORMATION: synthesized

<400> SEQUENCE: 1

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
```

-continued

```
                35                    40                    45

Glu Glu Val Lys Lys Ile Thr Ala Glu Arg His Gly Thr Val Val Thr
    50                    55                    60

Val Lys Arg Val Glu Lys Val Gln Lys Lys Phe Leu Gly Arg Pro Val
65                    70                    75                    80

Glu Val Trp Lys Leu Tyr Phe Thr His Pro Gln Asp Val Pro Ala Ile
                85                    90                    95

Arg Asp Lys Ile Arg Glu His Pro Ala Val Ile Asp Ile Tyr Glu Tyr
                100                   105                   110

Asp Ile Pro Phe Ala Lys Arg Tyr Leu Ile Asp Lys Gly Leu Val Pro
                115                   120                   125

Met Glu Gly Asn Glu Glu Leu Thr Phe Leu Ala Val Asp Ile Glu Thr
    130                   135                   140

Leu Tyr His Glu Gly Glu Glu Phe Gly Lys Gly Pro Ile Ile Met Ile
145                   150                   155                   160

Ser Tyr Ala Asp Glu Glu Gly Ala Lys Val Ile Thr Trp Lys Ser Ile
                165                   170                   175

Asp Leu Pro Tyr Val Glu Val Val Ser Ser Glu Arg Glu Met Ile Lys
                180                   185                   190

Arg Leu Val Lys Val Ile Arg Glu Lys Asp Pro Asp Val Ile Ile Thr
                195                   200                   205

Tyr Asn Gly Asp Asn Phe Asp Phe Pro Tyr Leu Leu Lys Arg Ala Glu
    210                   215                   220

Lys Leu Gly Ile Lys Leu Pro Leu Gly Arg Asp Asn Ser Glu Pro Lys
225                   230                   235                   240

Met Gln Arg Met Gly Asp Ser Leu Ala Val Glu Ile Lys Gly Arg Ile
                245                   250                   255

His Phe Asp Leu Phe Pro Val Ile Arg Arg Thr Ile Asn Leu Pro Thr
                260                   265                   270

Tyr Thr Leu Glu Ala Val Tyr Glu Ala Ile Phe Gly Lys Ser Lys Glu
                275                   280                   285

Lys Val Tyr Ala His Glu Ile Ala Glu Ala Trp Glu Thr Gly Lys Gly
    290                   295                   300

Leu Glu Arg Val Ala Lys Tyr Ser Met Glu Asp Ala Lys Val Thr Phe
305                   310                   315                   320

Glu Leu Gly Lys Glu Phe Phe Pro Met Glu Ala Gln Leu Ala Arg Leu
                325                   330                   335

Val Gly Gln Ser Leu Trp Asp Val Ser Arg Ser Ser Thr Gly Asn Leu
                340                   345                   350

Val Glu Trp Phe Leu Leu Arg Lys Ala Tyr Glu Arg Asn Glu Leu Ala
                355                   360                   365

Pro Asn Lys Pro Asp Glu Glu Glu Tyr Gln Arg Arg Leu Arg Glu Ser
    370                   375                   380

Tyr Thr Gly Gly Phe Val Lys Glu Pro Glu Lys Gly Leu Trp Glu Asn
385                   390                   395                   400

Ile Val Tyr Leu Asp Tyr Lys Ser Leu Tyr Pro Ser Ile Ile Ile Thr
                405                   410                   415

His Asn Val Ser Pro Asp Thr Leu Asn Leu Glu Gly Cys Lys Asn Tyr
                420                   425                   430

Asp Ile Ala Pro Gln Val Gly His Lys Phe Cys Lys Asp Ile Pro Gly
                435                   440                   445

Phe Ile Pro Ser Leu Leu Gly Asn Leu Leu Glu Glu Arg Gln Lys Ile
    450                   455                   460
```

```
Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Lys Tyr Ala Val Ile Asp Glu Glu Gly Lys Ile Thr Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Ala Leu Leu Lys Asp Gly Asp Val Glu Lys Ala
625                 630                 635                 640

Val Arg Ile Val Lys Glu Val Thr Glu Lys Leu Ser Lys Tyr Glu Val
                645                 650                 655

Pro Pro Glu Lys Leu Val Ile His Glu Gln Ile Thr Arg Asp Leu Lys
            660                 665                 670

Asp Tyr Lys Ala Thr Gly Pro His Val Ala Val Ala Lys Arg Leu Ala
            675                 680                 685

Ala Arg Gly Val Lys Ile Arg Pro Gly Thr Val Ile Ser Tyr Ile Val
        690                 695                 700

Leu Lys Gly Ser Gly Arg Ile Gly Asp Arg Ala Ile Pro Phe Asp Glu
705                 710                 715                 720

Phe Asp Pro Thr Lys His Lys Tyr Asp Ala Glu Tyr Tyr Ile Glu Asn
                725                 730                 735

Gln Val Leu Pro Ala Val Glu Arg Ile Leu Arg Ala Phe Gly Tyr Arg
            740                 745                 750

Lys Glu Asp Leu Arg Tyr Gln Lys Thr Arg Gln Val Gly Leu Ser Ala
            755                 760                 765

Trp Leu Lys Pro Lys Gly Thr
770                 775
```

```
<210> SEQ ID NO 2
<211> LENGTH: 2328
<212> TYPE: DNA
<213> ORGANISM: Artificial Sequence
<220> FEATURE:
<223> OTHER INFORMATION: synthesized

<400> SEQUENCE: 2
atgattctgg acaccgatta catcaccgaa gatggcaagc cagttatccg catttttcaaa        60 aaagagaatg gtgaattcaa gatcgaatat gatcgtacct tcgagccgta cttctatgct       120
ctgctgaaag acgatagcgc gattgaggag gtcaagaaaa tcaccgcgga gcgtcacggt       180
acggttgtta ccgtgaaacg cgtggagaaa gtccagaaga aatttctggg tcgcccggtt       240
```

```
gaagtgtgga agctgtactt tacgcatccg caagatgttc cggcgattcg cgataagatt    300
cgtgagcacc cggcagtcat tgacatctac gagtatgaca ttccgttcgc caagcgttat    360
ctgatcgata agggtctggt cccgatggag gggaacgagg agctaacgtt tctagccgtt    420
gatatagaaa cattgtacca tgaaggagag gagttcggga aagggccaat aataatgatc    480
agctacgccg acgaggaagg ggccaaggtg ataacttgga agagcataga cttaccttac    540
gttgaagtgg tttcgagcga gagggagatg ataaagaggc tcgtgaaggt aattagagag    600
aaagatcccg acgtgataat aacgtacaat ggtgataatt tcgactttcc gtacctctta    660
aagagggctg aaaagctcgg aataaagctc ccccttggaa gggacaatag cgagccgaaa    720
atgcagagga tggggggattc attagccgta gagataaagg gcagaataca cttcgattta    780
ttccccgtca taagaagaac gatcaacctt ccaacataca ccctcgaagc ggtttatgag    840
gctatatttg aaagtctaa ggagaaagtc tatgcccatg agatagctga ggcctgggaa    900
accgggaaag ggctagagag ggtagctaag tattcaatgg aagatgcgaa ggtaaccttt    960
gagctcggaa aggagttctt cccgatggaa gcccagctag ctaggctcgt tggccaaagc   1020
ctgtgggacg ttagccgcag cagcaccggt aacttagttg aatggttctt gctgcgtaag   1080
gcatacgaac gcaatgagct ggcgccgaac aaaccggacg aagaggagta tcaaagaagg   1140
ctcagggaga gctacacagg tggattcgtt aaagagccag aaaaggggtt gtgggaaaac   1200
atagtatacc tagattacaa atcactatat ccctcgatta taattaccca caatgtttct   1260
cccgatactc taaatcttga gggatgcaag aactatgata tcgctcctca agtaggccac   1320
aagttctgca aggacatccc tggtttcata ccaagcttac tgggtaacct actggaggag   1380
agacaaaaga taaaaagag aatgaaagaa agtaaagatc ccgtcgagaa gaaactcctt   1440
gattacagac agagagctat aaaaatactt gcaaacagct attatggcta ttatggatat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaaaaaga aatacgctgt tattgatgaa   1800
gagggcaaga tcacgacccg tggcctggaa attgtgcgcc gtgattggag cgaaattgca   1860
aaagaaacgc aagcgcgtgt gctggaagcg ctgctgaagg acggcgacgt cgaaaaagct   1920
gtgcgtattg ttaaagaggt caccgagaag ctgagcaaat acgaggtccc gccagagaaa   1980
ttggtgattc acgaacagat tacgcgtgac ctgaaagact ataaggccac cggtccgcat   2040
gtcgcagtgg cgaagcgcct ggcggctcgc ggtgtgaaga tccgtccggg taccgtcatt   2100
agctatatcg tgctgaaggg cagcggtcgt atcggcgacc gtgcgattcc gttcgacgaa   2160
tttgatccga ccaaacacaa atatgatgcg gaatactata ttgagaacca agtgctgcca   2220
gccgttgagc gtattctgcg cgccttcggt taccgcaagg aagatctgcg ttaccagaaa   2280
actcgtcagg tcggtctgtc cgcatggctg aaaccgaagg gcacctga                2328
```

<210> SEQ ID NO 3
<211> LENGTH: 771
<212> TYPE: PRT
<213> ORGANISM: Artificial Sequence
<220> FEATURE:
<223> OTHER INFORMATION: synthesized

<400> SEQUENCE: 3

-continued

```
Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
        50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
            115                 120                 125

Met Glu Gly Asn Glu Glu Leu Thr Phe Leu Ala Val Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
            195                 200                 205

Tyr Asn Gly Asp Asn Phe Asp Phe Pro Tyr Leu Leu Lys Arg Ala Glu
        210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
            275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415
```

-continued

```
His Asn Val Ser Pro Asp Thr Leu Asn Arg Glu Asn Cys Lys Glu Tyr
        420                 425                 430

Asp Val Ala Pro Gln Val Gly His Arg Phe Cys Lys Asp Phe Pro Gly
        435                 440                 445

Phe Ile Pro Ser Leu Leu Gly Asn Leu Leu Glu Glu Arg Gln Lys Ile
        450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
                515                 520                 525

Leu Glu Ser Arg Gly Phe Lys Val Leu Tyr Ile Asp Thr Asp Gly Leu
        530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
                580                 585                 590

Lys Tyr Ala Leu Ile Asp Glu Glu Gly Lys Ile Val Thr Arg Gly Leu
                595                 600                 605

Glu Ile Val Arg Arg Asp Trp Ser Glu Ile Ala Lys Glu Thr Gln Ala
        610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
                660                 665                 670

Tyr Lys Ala Ile Gly Pro His Val Ala Val Ala Lys Arg Leu Ala Ala
                675                 680                 685

Lys Gly Val Lys Val Lys Pro Gly Met Val Ile Gly Tyr Ile Val Leu
        690                 695                 700

Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
        740                 745                 750

Glu Asp Leu Lys Tyr Gln Lys Thr Lys Gln Val Gly Leu Gly Ala Trp
        755                 760                 765

Leu Lys Phe
    770
```

<210> SEQ ID NO 4
<211> LENGTH: 775
<212> TYPE: PRT
<213> ORGANISM: Artificial Sequence
<220> FEATURE:
<223> OTHER INFORMATION: synthesized

<400> SEQUENCE: 4

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Leu
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Arg Thr Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Tyr Lys Ser Leu Tyr Pro Ser Ile Ile Ile Thr
                405                 410                 415

His Asn Val Ser Pro Asp Thr Leu Asn Leu Glu Gly Cys Lys Asn Tyr
```

-continued

```
                420              425              430

Asp Ile Ala Pro Gln Val Gly His Lys Phe Cys Lys Asp Ile Pro Gly
        435              440              445

Phe Ile Pro Ser Leu Leu Gly His Leu Leu Glu Glu Arg Gln Lys Ile
        450              455              460

Lys Thr Lys Met Lys Glu Thr Gln Asp Pro Ile Glu Lys Ile Leu Leu
465              470              475              480

Asp Tyr Arg Gln Lys Ala Ile Lys Leu Leu Ala Asn Ser Phe Tyr Gly
            485              490              495

Tyr Tyr Gly Tyr Ala Lys Ala Arg Trp Tyr Cys Lys Glu Cys Ala Glu
            500              505              510

Ser Val Thr Ala Trp Gly Arg Lys Tyr Ile Glu Leu Val Trp Lys Glu
            515              520              525

Leu Glu Glu Lys Phe Gly Phe Lys Val Leu Tyr Ile Asp Thr Asp Gly
        530              535              540

Leu Tyr Ala Thr Ile Pro Gly Gly Glu Ser Glu Glu Ile Lys Lys Lys
545              550              555              560

Ala Leu Glu Phe Val Lys Tyr Ile Asn Ser Lys Leu Pro Gly Leu Leu
            565              570              575

Glu Leu Glu Tyr Glu Gly Phe Tyr Lys Arg Gly Phe Phe Val Thr Lys
            580              585              590

Lys Arg Tyr Ala Val Ile Asp Glu Glu Gly Lys Val Ile Thr Arg Gly
            595              600              605

Leu Glu Ile Val Arg Arg Asp Trp Ser Glu Ile Ala Lys Glu Thr Gln
        610              615              620

Ala Arg Val Leu Glu Thr Ile Leu Lys His Gly Asp Val Glu Glu Ala
625              630              635              640

Val Arg Ile Val Lys Glu Val Ile Gln Lys Leu Ala Asn Tyr Glu Ile
            645              650              655

Pro Pro Glu Lys Leu Ala Ile Tyr Glu Gln Ile Thr Arg Pro Leu His
            660              665              670

Glu Tyr Lys Ala Ile Gly Pro His Val Ala Val Ala Lys Lys Leu Ala
            675              680              685

Ala Lys Gly Val Lys Ile Lys Pro Gly Met Val Ile Gly Tyr Ile Val
            690              695              700

Leu Arg Gly Asp Gly Pro Ile Ser Asn Arg Ala Ile Leu Ala Glu Glu
705              710              715              720

Tyr Asp Pro Lys Lys His Lys Tyr Asp Ala Glu Tyr Tyr Ile Glu Asn
            725              730              735

Gln Val Leu Pro Ala Val Leu Arg Ile Leu Glu Gly Phe Gly Tyr Arg
            740              745              750

Lys Glu Asp Leu Arg Tyr Gln Lys Thr Arg Gln Val Gly Leu Thr Ser
            755              760              765

Trp Leu Asn Ile Lys Lys Ser
        770              775
```

```
<210> SEQ ID NO 5
<211> LENGTH: 774
<212> TYPE: PRT
<213> ORGANISM: Artificial Sequence
<220> FEATURE:
<223> OTHER INFORMATION: synthesized

<400> SEQUENCE: 5

Met Ile Leu Asp Thr Asp Tyr Ile Thr Glu Asp Gly Lys Pro Val Ile
```

-continued

```
1              5                  10                 15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
                35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
                115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
                180                 185                 190

Arg Phe Leu Arg Val Val Lys Glu Lys Asp Pro Asp Val Leu Ile Thr
                195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
    275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430
```

```
Val Ala Pro Gln Val Gly His Arg Phe Cys Lys Asp Phe Pro Gly Phe
        435             440             445

Ile Pro Ser Leu Leu Gly Asp Leu Leu Glu Glu Arg Gln Lys Ile Lys
        450             455             460

Lys Lys Met Lys Ala Thr Ile Asp Pro Ile Glu Arg Lys Leu Leu Asp
465             470             475             480

Tyr Arg Gln Arg Ala Ile Lys Ile Leu Ala Asn Ser Tyr Tyr Gly Tyr
                485             490             495

Tyr Gly Tyr Ala Arg Ala Arg Trp Tyr Cys Lys Glu Cys Ala Glu Ser
            500             505             510

Val Thr Ala Trp Gly Arg Glu Tyr Ile Thr Met Thr Ile Lys Glu Ile
        515             520             525

Glu Glu Lys Tyr Gly Phe Lys Val Ile Tyr Ser Asp Thr Asp Gly Phe
        530             535             540

Phe Ala Thr Ile Pro Gly Ala Asp Ala Glu Thr Val Lys Lys Lys Ala
545             550             555             560

Met Glu Phe Leu Lys Tyr Ile Asn Ala Lys Leu Pro Gly Ala Leu Glu
                565             570             575

Leu Glu Tyr Glu Gly Phe Tyr Lys Arg Gly Phe Phe Val Thr Lys Lys
            580             585             590

Lys Tyr Ala Val Ile Asp Glu Glu Gly Lys Ile Thr Thr Arg Gly Leu
        595             600             605

Glu Ile Val Arg Arg Asp Trp Ser Glu Ile Ala Lys Glu Thr Gln Ala
        610             615             620

Arg Val Leu Glu Ala Leu Leu Lys Asp Gly Asp Val Glu Lys Ala Val
625             630             635             640

Arg Ile Val Lys Glu Val Thr Glu Lys Leu Ser Lys Tyr Glu Val Pro
                645             650             655

Pro Glu Lys Leu Val Ile His Glu Gln Ile Thr Arg Asp Leu Lys Asp
            660             665             670

Tyr Lys Ala Thr Gly Pro His Val Ala Val Ala Lys Arg Leu Ala Ala
        675             680             685

Arg Gly Val Lys Ile Arg Pro Gly Thr Val Ile Ser Tyr Ile Val Leu
        690             695             700

Lys Gly Ser Gly Arg Ile Gly Asp Arg Ala Ile Pro Phe Asp Glu Phe
705             710             715             720

Asp Pro Thr Lys His Lys Tyr Asp Ala Glu Tyr Tyr Ile Glu Asn Gln
                725             730             735

Val Leu Pro Ala Val Glu Arg Ile Leu Arg Ala Phe Gly Tyr Arg Lys
            740             745             750

Glu Asp Leu Arg Tyr Gln Lys Thr Arg Gln Val Gly Leu Ser Ala Trp
        755             760             765

Leu Lys Pro Lys Gly Thr
    770
```

```
<210> SEQ ID NO 6
<211> LENGTH: 2316
<212> TYPE: DNA
<213> ORGANISM: Artificial Sequence
<220> FEATURE:
<223> OTHER INFORMATION: synthesized

<400> SEQUENCE: 6
atgataatcg atgctgatta cataacggaa gatggcaagc cgataataag gatattcaaa        60
```

```
aaggaaaagg gagagtttaa ggtagaatac gataggacgt ttagacccta catttatgct    120
cttttaaagg atgattcggc catagatgag gttaagaaga taaccgccga gaggcacgga    180
aagatagtca ggataaccga ggttgagaaa gtccagaaga aattcctagg aaggccaata    240
gaagtctgga agctctatct tgagcatccc caggatgttc cagccataag agagaagata    300
agggaacatc cagctgtagt tgatatattt gaatacgaca taccctttgc gaagcgctac    360
ctcatagaca agggattgac tccaatggag gggaacgagg agctaacgtt tctagccgtt    420
gatatagaaa cattgtacca tgaaggagag gagttcggga aagggccaat aataatgatc    480
agctacgccg acgaggaagg ggccaaggtg ataacttgga agagcataga cttaccttac    540
gttgaagtgg tttcgagcga gagggagatg ataaagaggc tcgtgaaggt aattagagag    600
aaagatcccg acgtgataat aacgtacaat ggtgataatt cgactttcc gtacctctta    660 aagagggctg aaaagctcgg aataaagctc ccccttggaa gggacaatag cgagccgaaa    720
atgcagagga tggggggattc attagccgta gagataaagg gcagaataca cttcgattta    780
ttccccgtca taagaagaac gatcaacctt ccaacataca ccctcgaagc ggtttatgag    840
gctatatttg gaaagtctaa ggagaaagtc tatgcccatg agatagctga ggcctgggaa    900
accgggaaag ggctagagag ggtagctaag tattcaatgg aagatgcgaa ggtaaccttt    960
gagctcggaa aggagttctt cccgatggaa gcccagctag ctaggctcgt tggccagcca   1020
gtttgggacg tttcaaggtc gagcaccgga aacctcgttg agtggtttct ccttaggaag   1080
gcctacgaga gaaatgagct cgcgcccaat aaaccggacg agagggaata cgagagaagg   1140
ctaagagaga gctatgaagg gggttacgtt aaggagccag agaagggatt gtgggaaggg   1200
atagtcagct tagactttag gtccctatat ccctctataa ttataactca caacgtctca   1260
ccagacactt tgaatagaga aaattgcaag gaatatgacg ttgcccccca agtggggcac   1320
agattctgca aggatttccc aggattcata ccaagcttac tgggtaacct actggaggag   1380
agacaaaaga taaaaaagag aatgaaagaa agtaaagatc ccgtcgagaa gaaactcctt   1440
gattacagac agagagctat aaaaatactt gcaaacagct attatggcta ttatggatat   1500
gcaaaggcca gatggtactg taaagagtgt gcagagagc taaccgcatg gggaaggcag   1560
tacatagacc tggttaggag ggaacttgag agcagaggat ttaaagttct ctacatagac   1620
acagatggcc tctacgcaac gattcctgga gccaagcatg aggaaataaa agagaaggca   1680
ttgaagttcg tcgagtacat aaactccaag ttacctgggc ttcttgaatt ggaatacgaa   1740
ggtttctacg cgagagggtt cttcgtgacg aagaaaaagt acgcactaat cgacgaggaa   1800
ggaaagatag ttacgagggg gctcgaaata gtaaggagag attggagtga aatagcaaag   1860
gagacccagg ccaaggttct tgaggcaata ctcaagcacg gtaacgttga tgaggccgta   1920
aaaatagtaa aggaggttac agaaaaactc agtaaatatg aaataccacc cgaaaagctt   1980
gtaatttatg agcagataac gaggcctctg agcgagtata aagcgatagg ccctcacgtt   2040
gcagtagcta aaaggctcgc agcgaaggga gtaaaagtta agccagggat ggttatcggt   2100
tacatagttt tgagggga cgggccaata agcaagaggg ccatagctat agaggagttc   2160
gatcccaaaa agcataagta cgatgccgaa tactacatag agaaccaagt tctgccagcg   2220
gtggagagga tattgagagc atttggttat cgcaaggagg atttgaagta tcaaaaaact   2280
aaacaagtgg gccttggagc atggcttaag ttctga                            2316
```

<210> SEQ ID NO 7
<211> LENGTH: 2328

<212> TYPE: DNA
<213> ORGANISM: Artificial Sequence
<220> FEATURE:
<223> OTHER INFORMATION: synthesized

<400> SEQUENCE: 7

```
atgattttag atgtggatta cataactgaa gaaggaaaac ctgttattag gctattcaaa         60
aaagagaacg gaaaatttaa gatagagcat gatagaactt ttagaccata catttacgct        120
cttctcaggg atgattcaaa gattgaagaa gttaagaaaa taacggggga aaggcatgga        180
aagattgtga gaattgttga tgtagagaag gttgagaaaa agtttctcgg caagcctatt        240
accgtgtgga aactttattt ggaacatccc caagatgttc ccactttaag agaaaaagtt        300
agagaacatc cagcagttgt ggacatcttc gaatacgata ttccatttgc aaagagatac        360
ctcatcgaca aaggcctaat accaatggag ggggaagaag agctaaagat tcttgccttc        420
gatatagaaa ccctctatca cgaaggagaa gagtttggaa aaggcccaat tataatgatt        480
agttatgcag atgaaaatga agcaagggtg attacttgga aaaacataga tcttccatac        540
gttgagtcag tatcaaccga gaaagagatg ataaagagat ttctcaggat tatcagggag        600
aaggatcctg acattatagt tacttataat ggagactcat tcgacttccc atatttagcg        660
aaaagggcag aaaaacttgg gattaaatta accattggaa gagatggaag cgagcccaag        720
atgcagagaa taggcgatat gacggctgta gaagtcaagg gaagaataca tttcgacttg        780
tatcatgtaa taaggacaac aataaatctc ccaacataca cactagaggc tgtatatgaa        840 gcaattttg gaaagccaaa ggagaaggta tacgccgacg agatagcaaa agcctgggaa         900
agtggagaga accttgagag agttgccaaa tactcgatgg aagatgcaaa ggcaacttat        960
gaactcggga agaattcct tccaatggaa attcagcttt caagattagt tggacaacct       1020
ttatgggatg tttcaaggtc aagcacaggg aaccttgtag agtggttctt acttaggaaa       1080
gcctacgaaa gaaacgaagt agctccaaac aagccaagtg aagaggagta tcaaagaagg       1140
ctcagggaga gctacacagg tggattcgtt aaagagccag aaaaggggtt gtgggaaaac       1200
atagtatacc tagattacaa atcactatat ccctcgatta taattaccca caatgtttct       1260
cccgatactc taaatcttga gggatgcaag aactatgata tcgctcctca gtaggccac        1320 aagttctgca aggacatccc tggtttttata ccaagtctct tgggacattt gttagaggaa       1380
agacaaaaga ttaagacaaa aatgaaggaa actcaagatc ctatagaaaa aatactcctt       1440
gactatagac aaaaagcgat aaaactctta gcaattctt tctacggata ttatggctat        1500
gcaaaagcaa gatggtactg taaggagtgt gctgagagcg ttactgcctg gggaagaaag       1560
tacatcgagt tagtatggaa ggagctcgaa gaaaagtttg gatttaaagt cctctacatt       1620
gacactgatg gtctctatgc aactatccca ggaggagaaa gtgaggaaat aaagaaaaag       1680
gctctagaat ttgtaaaata cataaattca aagctccctg gactgctaga gcttgaatat       1740
gaagggtttt ataagagggg attcttcgtt acgaagaaga ggtatgcagt aatagatgaa       1800
gaaggaaaag tcattactcg tggtttagag atagttagga gagattggag tgaaattgca       1860
aaagaaactc aagctagagt tttggagaca atactaaaac acggagatgt tgaagaagct       1920
gtgagaatag taaaagaagt aatacaaaag cttgccaatt atgaaattcc accagagaag       1980
ctcgcaatat atgagcagat aacaagacca ttacatgagt ataaggcgat aggtcctcac       2040
gtagctgttg caaagaaact agctgctaaa ggagttaaaa taaagccagg aatggtaatt       2100
ggatacatag tacttagagg cgatggtcca attagcaata gggcaattct agctgaggaa       2160
```

-continued

```
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatcctga                 2328

<210> SEQ ID NO 8
<211> LENGTH: 2325
<212> TYPE: DNA
<213> ORGANISM: Artificial Sequence
<220> FEATURE:
<223> OTHER INFORMATION: synthesized

<400> SEQUENCE: 8
atgattctgg acaccgatta catcaccgaa gatggcaagc cagttatccg cattttcaaa      60
aaagagaatg gtgaattcaa gatcgaatat gatcgtacct tcgagccgta cttctatgct     120
ctgctgaaag acgatagcgc gattgaggag gtcaagaaaa tcaccgcgga gcgtcacggt     180
acggttgtta ccgtgaaacg cgtggagaaa gtccagaaga aatttctggg tcgcccggtt     240
gaagtgtgga agctgtactt tacgcatccg caagatgttc cggcgattcg cgataagatt     300
cgtgagcacc cggcagtcat tgacatctac gagtatgaca ttccgttcgc caagcgttat     360
ctgatcgata agggtctggt cccgatggag ggtgacgaag aactgaagat gctggcgttc     420
gacatcgaaa ctctgtacca cgagggtgaa gagtttgccg agggtccgat cttgatgatt     480
tcctacgcgg acgaagaggg cgcacgtgtt atcacgtgga aaaatgttga tctgccgtat     540
gttgacgtcg taagcaccga gcgtgagatg atcaaacgtt ttctgcgcgt tgttaaagaa     600
aaagatcctg acgtgctgat cacctacaac ggtgacaatt cgatttcgc gtacctgaag      660 aaacgttgcg aaaaactggg tattaacttc gcgctgggtc gcgatggctc tgaaccgaag     720
atccagcgca tgggtgatcg tttttgcggtc gaggtgaagg gtcgcattca tttcgacctg    780
tacccggtga ttcgtcgtac catcaacttg ccgacttaca ccctggaagc cgtctatgaa     840
gctgtatttg gtcaaccgaa agaaaaagtg tacgctgagg aaattacgac ggcgtgggaa     900
accggtgaga acctggagcg cgttgcacgt tattctatgg aggacgcgaa agttacctac     960
gaactgggta agagttcct gccgatggag gcccaactgt cccgtctgat cggccaaagc     1020
ctgtgggacg ttagccgcag cagcaccggt aacttagttg aatggttctt gctgcgtaag    1080
gcatacgaac gcaatgagct ggcgccgaac aaaccggacg agaaagaatt ggcgcgtcgc    1140
cgccagagct atgagggtgg ttatgtcaaa gaaccggagc gcggcttgtg ggagaacatc    1200
gtctatttgg attttcgtag cctgtacccg agcatcatta tcacgcataa tgtgagcccg    1260
gatacgttga tcgtgagggt ctgtaaggaa tacgacgtgg cgcctcaggt tggccaccgt    1320
ttctgcaagg actttccggg ctttatcccg agcctgctgg gtgatttgct ggaggaacgt    1380
cagaaaatca gaagaagat gaaagcaacc attgatccga tcgagcgcaa attactggac    1440
taccgtcaac gtgccatcaa gatcctggcg aattcgtatt atggttacta tggctacgcg    1500
cgtgcgcgct ggtattgcaa agagtgtgcc gagagcgtga ccgcttgggg tcgtgagtac    1560
attaccatga cgatcaaaga gattgaagag aaatacggct ttaaggttat ctatagcgac    1620
accgacggtt tctttgcaac tatccctggc gcagacgcag aaaccgttaa gaaaaaggca    1680
atggagtttc tgaagtatat caacgcgaag ttgccaggcg ccctggaact ggagtacgag    1740
ggcttctaca gcgtggcctt tttcgtgacg aaaaagaaat acgctgttat tgatgaagag    1800
ggcaagatca cgaccgtgg cctggaaatt gtgcgccgtg attggagcga aattgcaaaa    1860
gaaacgcaag cgcgtgtgct ggaagcgctg ctgaaggacg cgacgtcga aaaagctgtg    1920
```

-continued

```
cgtattgtta aagaggtcac cgagaagctg agcaaatacg aggtcccgcc agagaaattg    1980
gtgattcacg aacagattac gcgtgacctg aaagactata aggccaccgg tccgcatgtc    2040
gcagtggcga agcgcctggc ggctcgcggt gtgaagatcc gtccgggtac cgtcattagc    2100
tatatcgtgc tgaagggcag cggtcgtatc ggcgaccgtg cgattccgtt cgacgaattt    2160
gatccgacca aacacaaata tgatgcggaa tactatattg agaaccaagt gctgccagcc    2220
gttgagcgta ttctgcgcgc cttcggttac cgcaaggaag atctgcgtta ccagaaaact    2280
cgtcaggtcg gtctgtccgc atggctgaaa ccgaagggca cctga             2325

<210> SEQ ID NO 9
<211> LENGTH: 35
<212> TYPE: DNA
<213> ORGANISM: Artificial Sequence
<220> FEATURE:
<223> OTHER INFORMATION: synthesized

<400> SEQUENCE: 9
cctctgtcgt ttcctttctc tgtttttgtc cgtgg                              35

<210> SEQ ID NO 10
<211> LENGTH: 35
<212> TYPE: DNA
<213> ORGANISM: Artificial Sequence
<220> FEATURE:
<223> OTHER INFORMATION: synthesized

<400> SEQUENCE: 10
cgtctgttca tcgtcgtggc ggcccataat aatct                             35

<210> SEQ ID NO 11
<211> LENGTH: 34
<212> TYPE: DNA
<213> ORGANISM: Artificial Sequence
<220> FEATURE:
<223> OTHER INFORMATION: synthesized

<400> SEQUENCE: 11
gcactctttc tcgtaggtac tcagtccggc ttct                              34

<210> SEQ ID NO 12
<211> LENGTH: 32
<212> TYPE: DNA
<213> ORGANISM: Artificial Sequence
<220> FEATURE:
<223> OTHER INFORMATION: synthesized

<400> SEQUENCE: 12
cgggaatacg acggttaccc accacaagca cg                                32

<210> SEQ ID NO 13
<211> LENGTH: 17
<212> TYPE: DNA
<213> ORGANISM: Artificial Sequence
<220> FEATURE:
<223> OTHER INFORMATION: synthesized

<400> SEQUENCE: 13
gttttcccag tcacgac                                                 17

<210> SEQ ID NO 14
<211> LENGTH: 21
<212> TYPE: DNA
```

-continued

```
<213> ORGANISM: Artificial Sequence
<220> FEATURE:
<223> OTHER INFORMATION: synthesized

<400> SEQUENCE: 14
ggtatcttta tagtcctgtc g                                             21

<210> SEQ ID NO 15
<211> LENGTH: 20
<212> TYPE: DNA
<213> ORGANISM: Artificial Sequence
<220> FEATURE:
<223> OTHER INFORMATION: synthesized

<400> SEQUENCE: 15
agagtttgat cmtggctcag                                               20

<210> SEQ ID NO 16
<211> LENGTH: 20
<212> TYPE: DNA
<213> ORGANISM: Artificial Sequence
<220> FEATURE:
<223> OTHER INFORMATION: synthesized

<400> SEQUENCE: 16
cggttacctt gttacgactt                                               20
```

CHIMERIC DNA POLYMERASE AND APPLICATION THEREOF

INCORPORATION BY REFERENCE

The ASCII plain text file entitled 980P002_ST25.txt dated Oct. 24, 2023 and having a size of 40,000 bytes containing a Sequence Listing is hereby incorporated by reference.

FIELD

The present disclosure relates to the field of biology. In particular, the present disclosure relates to a chimeric DNA polymerase and application thereof.

BACKGROUND

DNA polymerases are enzymes for replicating and synthesizing a new DNA strand complementary to the sequence of the template from a 5'-end by using a single DNA strand as a template and four deoxynucleotides as substrates. The DNA polymerase can add free sqnucleotides to an 3'-end of the newly formed strand to elongate the new strand in a direction from 5'-end to 3'-end. Certain enzymes with 3'-to-5' exoribonuclease activity can correct errors in the newly synthesized DNA. During PCR amplification, the enzymes can cut a mismatched base, when it is produced, and thereafter, the polymerase can re-insert a correct base and continue the replication, thereby ensuring the accuracy of amplification. The enzymes with the correcting function have a lower error rate than ordinary DNA polymerases (such as Taq DNA polymerase), and are suitable for experiments that require high PCR fidelity, for example, gene screening, sequencing, mutation detection, etc.

DNA polymerases are mainly divided into six families: A, B, C, D, X, and Y. At present, the known thermostable DNA polymerases all belong to the family A or the family B. DNA polymerases belonging to the family A are all derived from eubacteria, for example, *Thermus aquaticus* (Taq), *Thermus thermophilus* (Tth), *Thermus caldophilus* (Tca), *Thermus flavus* (Tfl), and *Thermus filiformis* (Tfi) from the genus *Thermus*, and *Bacillus stearothemophilis* (Bst) from the genus *Bacillus*. The thermostable DNA polymerases belonging to the family B are all derived from archaea, for example, *Thermococcus litoralis* (Tli) from the genus *Thermococcus*, *Pyrococcus furiosus* (Pfu), *Thermococcus kodacaraensis* (KOD1), *Pyrococcus woesei* (Pwo), *Thermococcus gorgonarius* (Tgo) and *Pyrococcus abyssi* (Pab) from the genus *Thermococcu*, etc.

The amino acid sequence of a polymerase is the basis for the functional structure of the polymerase. Based on the structure-function analysis of a DNA polymerase, the various functions of the DNA polymerase, such as catalytic activity, correcting, nucleotide transfer, substrate binding, etc., have been assigned to various domains. As an example, the archaeal DNA polymerase is usually divided into five domains, i.e., an N-end domain, an exonucleolytic domain, a palm domain, a finger domain, and a thumb domain. It is generally believed that the activity of DNA polymerase involves the palm domain, the finger domain and the thumb domain. The palm domain is a catalytic site of the polymerase. The thumb domain interacts with newly synthesized dsDNA and interacts with the introduced nucleotides. The finger domain plays a role in the template immobilization and nucleotide specificity. The exonucleolytic domain is associated with either 5'-to-3' exonucleolytic activity or 3'-to-5' exonucleolytic activity or associated with both activities, and thus it is used to remove erroneously inserted bases. The domains of the DNA polymerase cooperate closely with each other to complete the whole process of DNA amplification.

However, it is necessary to further study the current DNA polymerases.

SUMMARY

The present disclosure aims to solve at least one of the technical problems existing in the prior art to a certain extent. To this end, the present disclosure provides a chimeric DNA polymerase, a method for obtaining the chimeric DNA polymerase, an isolated nucleic acid, a construct, a recombinant cell or recombinant microorganism, a kit, and applications thereof. The chimeric DNA polymerase has various properties such as high processivity and elongation rate, thermal stability, strong resistance to salts, high fidelity, etc., and thus they can meet the requirements of DNA amplification, synthesis, detection, sequencing, etc., having a wide application prospect.

It should be noted that the present disclosure is based on Applicant's following findings.

Currently, the advantages of DNA polymerases with the correcting function are offset by their relatively low processivity, which may result in a reduced yield of DNA amplification products. Taq DNA polymerase, as a representative of the DNA polymerases in the family A, has a relatively high amplification efficiency but lacks of fidelity. KOD/Pfu DNA polymerases, as representatives of the DNA polymerases in the family B, have disadvantages in that the high processivity is accompanied with the high fidelity.

In view of this, Applicant combined heterologous domains from different DNA polymerases to form a chimeric DNA polymerase, in order to form a specific spatial structure and exhibit corresponding functional characteristics by utilizing the unique interactions within each of different heterologous domains and between the different heterologous domains when these domains are fused. Specifically, Applicant studied 7 types of DNA polymerases, i.e., *Pyrococcus furiosus* (Pfu), *Thermococcus kodacaraensis* (KOD), *Pyrococcus woesei* (Pwo), *Thermococcus gorgonarius* (Tgo), *Pyrococcus abyssi* (Pab), *Pyrococcus* species GB-D (Deep vent), and *Thermococcus* sp. 9°N-7 (9°N), and 5 types of domains of each one of these DNA polymerases, to select chimeric DNA polymerases having the performances such as high processivity, high elongation rate, thermal stability, resistance to salts, and high fidelity, etc., which can meet the requirements of DNA amplification, synthesis, detection, sequencing, etc., thereby having a wide application prospect.

To this end, in an aspect of the present disclosure, the present disclosure provides a chimeric DNA polymerase. According to an embodiment of the present disclosure, the chimeric DNA polymerase includes: a first peptide fragment having at least 80% homology to at least one part of an amino acid sequence in an N-end domain of a KOD DNA polymerase; a second peptide fragment having at least 80% homology to at least one part of an amino acid sequence in an exonucleolytic domain of a Pab DNA polymerase, an N-end of the second peptide fragment being connected to a C-end of the first peptide fragment; a third peptide fragment having at least 80% homology to at least part of amino acids in the N-end domain of the KOD DNA polymerase, an N-end of the third peptide fragment being connected to a C-end of the second peptide fragment; a fourth peptide fragment having at least 80% homology to at least part of amino acids in a palm domain of a Pfu DNA polymerase, an N-end of the fourth peptide fragment being connected to a C-end of the third peptide fragment; a fifth peptide fragment having at least 80% homology to at least part of amino acids in a finger domain of the Pab DNA polymerase, an N-end of the fifth peptide fragment being connected to a C-end of the fourth peptide fragment; a sixth peptide fragment having at least 80% homology to at least part of the amino acids in the palm domain of the Pfu DNA polymerase, an N-end of the sixth peptide fragment being connected to a C-end of the fifth peptide fragment; and a seventh peptide fragment having at least 80% homology to at least part of amino acids in a thumb domain of the KOD DNA polymerase, an N-end of the seventh peptide fragment being connected to a C-end of the sixth peptide fragment.

Based on 7 types of DNA polymerases, i.e., *Pyrococcus furiosus* (Pfu), *Thermococcus kodacaraensis* (KOD), *Pyrococcus woesei* (Pwo), *Thermococcus gorgonarius* (Tgo), *Pyrococcus abyssi* (Pab), *Pyrococcus* species GB-D (Deep vent), and *Thermococcus* sp. 9°N-7 (9° N), and 5 types of domains of each of these DNA polymerases, Applicant has screened out the chimeric DNA polymerases having the performances such as high processivity, high elongation rate, thermal stability, resistance to salts, and high fidelity, etc., which can meet the requirement of DNA amplification, synthesis, detection, sequencing, etc., thereby having a wide application prospect.

According to an embodiment of the present disclosure, the chimeric DNA polymerase may further have the following additional technical features.

According to an embodiment of the present disclosure, the first peptide fragment has at least 80% homology to an amino acid sequence of sites 1 to 130 of the KOD DNA polymerase.

According to an embodiment of the present disclosure, the second peptide fragment has at least 80% homology to an amino acid sequence of sites 131 to 337 of the Pab DNA polymerase.

According to an embodiment of the present disclosure, the third peptide fragment has at least 80% homology to an amino acid sequence of sites 338 to 373 of the KOD DNA polymerase.

According to an embodiment of the present disclosure, the fourth peptide fragment has at least 80% homology to an amino acid sequence of sites 374 to 448 of the Pfu DNA polymerase.

According to an embodiment of the present disclosure, the fifth peptide fragment has at least 80% homology to an amino acid sequence of sites 449 to 500 of the Pab DNA polymerase.

According to an embodiment of the present disclosure, the sixth peptide fragment has at least 80% homology to an amino acid sequence of sites 501 to 591 of the Pfu DNA polymerase.

According to an embodiment of the present disclosure, the seventh peptide fragment has at least 80% homology to an amino acid sequence of sites 591 to 774 of the KOD DNA polymerase.

According to an embodiment of the present disclosure, the chimeric DNA polymerase has an amino acid sequence set forth as SEQ ID NO: 1.

In another aspect of the present disclosure, the present disclosure provides an isolated nucleic acid. According to an embodiment of the present disclosure, the isolated nucleic acid encodes the aforementioned chimeric DNA polymerase. Therefore, the isolated nucleic acid according to the embodiment of the present disclosure can be used to encode the chimeric DNA polymerases having the performances such as high processivity, high elongation rate, thermal stability, strong resistance to salts, and high fidelity, etc., which can meet the requirements of DNA amplification, synthesis, detection, sequencing, etc., thereby having a wide application prospect.

According to an embodiment of the present disclosure, the isolated nucleic acid has a nucleotide sequence set forth as SEQ ID NO: 2.

In yet another aspect of the present disclosure, the present disclosure provides a construct. According to an embodiment of the present disclosure, the construct contains the isolated nucleic acid as described above. Thus, the construct according to the embodiment of the present disclosure can express the chimeric DNA polymerases having all the performances such as high processivity, high elongation rate, thermal stability, strong resistance to salts, and high fidelity, etc., which can meet the requirements of DNA amplification, synthesis, detection, sequencing, etc., thereby having a wide application prospect.

In yet another aspect of the present disclosure, the present disclosure provides a recombinant cell or recombinant microorganism. According to an embodiment of the present disclosure, the recombinant cell or recombinant microorganism contains the isolated nucleic acid as described above. Thus, the recombinant cell or recombinant microorganism according to the embodiment of the present disclosure can express the chimeric DNA polymerases all the performances such as high processivity, high elongation rate, thermal stability, strong resistance to salts, and high fidelity, etc., which can meet the requirements of DNA amplification, synthesis, detection, sequencing, etc., thereby having a wide application prospect.

In yet another aspect of the present disclosure, the present disclosure provides a method for obtaining the aforementioned chimeric DNA polymerase. According to an embodiment of the present disclosure, the method comprises: culturing the aforementioned recombinant cell or recombinant microorganism under conditions suitable for expressing the chimeric DNA polymerase, to obtain the chimeric DNA polymerase. Thus, the method according to the embodiment of the present disclosure can obtain the chimeric DNA polymerase all the performances such as high processivity, high elongation rate, thermal stability, strong resistance to salts, and high fidelity, etc., which can meet the requirements of DNA amplification, synthesis, detection, sequencing, etc., thereby having a wide application prospect.

In yet another aspect of the present disclosure, the present disclosure provides a kit. According to an embodiment of the present disclosure, the kit contains the aforementioned chimeric DNA polymerase, isolated nucleic acid, construct, recombinant cell, or recombinant microorganism. Therefore, the use of the kit according to the embodiment of the present disclosure to amplify DNA has the advantages such as high amplification product yield and high amplification accuracy, and is suitable for massive production and wide application.

In yet another aspect of the present disclosure, the present disclosure provides uses of the aforementioned chimeric DNA polymerase, isolated nucleic acid, construct, recombinant cell or recombinant microorganism, or kit in DNA amplification. Thus, the DNA amplification has the advantages such as high amplification product yield and high amplification accuracy, and is suitable for wide production and application.

According to an embodiment of the present disclosure, the chimeric DNA polymerase, the isolated nucleic acid, the construct, the recombinant cell or recombinant microorganism, or the kit is used for gene screening, sequencing or mutation detection.

Additional aspects and advantages of the present disclosure will be in part provided in the following description, or they will be become apparent from the following description, or they can be learned by practice of the present disclosure.

BRIEF DESCRIPTION OF DRAWINGS

The above and/or additional aspects and advantages of the present disclosure will become apparent and readily understood from the following description of embodiments in conjunction with the accompanying drawings, in which.

DESCRIPTION OF EMBODIMENTS

Figure 1:
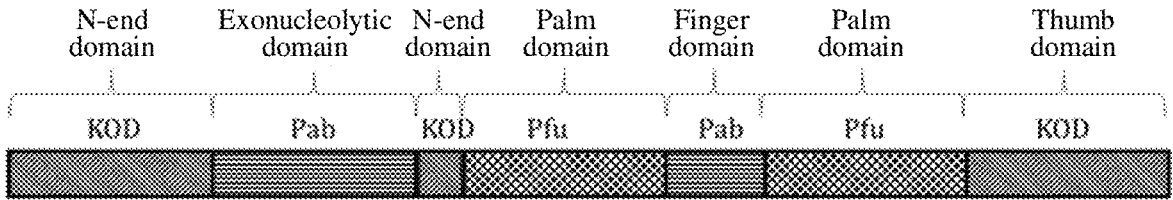
FIG. 1 is a schematic structural diagram of a chimeric DNA polymerase according to an embodiment of the present disclosure.

Embodiments of the present disclosure are described in detail below. The embodiments described below are merely illustrative for explaining the present disclosure, and they should not be construed as limiting the present disclosure.

It should be noted that the terms "first" and "second" are only used for descriptive purposes, and cannot be understood as indicating or implying relative importance or implying the number of indicated technical features. Thus, a feature defined by "first" or "second" may expressly or implicitly include one or more of the features. Further, in the description of the present disclosure, "plurality" means two or more, unless otherwise specified.

The present disclosure provides a chimeric DNA polymerase, a method for obtaining the chimeric DNA polymerase, an isolated nucleic acid, a construct, a recombinant cell or recombinant microorganism, a kit, and applications thereof, which will be described in detail below.

Chimeric DNA Polymerase

In one aspect of the present disclosure, the present disclosure provides a chimeric DNA polymerase. According to an embodiment of the present disclosure, the chimeric DNA polymerase incudes: a first peptide fragment having at least 80% homology to at least one part of an amino acid sequence in an N-end domain of a KOD DNA polymerase; a second peptide fragment having at least 80% homology to at least one part of an amino acid sequence in an exonucleolytic domain of a Pab DNA polymerase, an N-end of the second peptide fragment being connected to a C-end of the first peptide fragment; a third peptide fragment having at least 80% homology to at least part of amino acids in the N-end domain of the KOD DNA polymerase, an N-end of the third peptide fragment being connected to a C-end of the second peptide fragment; a fourth peptide fragment having at least 80% homology to at least part of amino acids in a palm domain of a Pfu DNA polymerase, an N-end of the fourth peptide fragment being connected to a C-end of the third peptide fragment; a fifth peptide fragment having at least 80% homology to at least part of amino acids in a finger domain of the Pab DNA polymerase, an N-end of the fifth peptide fragment being connected to a C-end of the fourth peptide fragment; a sixth peptide fragment having at least 80% homology to at least part of the amino acids in the palm domain of the Pfu DNA polymerase, an N-end of the sixth peptide fragment being connected to a C-end of the fifth peptide fragment; and a seventh peptide fragment having at least 80% homology to at least part of amino acids in a thumb domain of the KOD DNA polymerase, an N-end of the seventh peptide fragment being connected to a C-end of the sixth peptide fragment.

In order to develop a DNA polymerase with high processivity and improved fidelity, Applicant focused on the DNA polymerases with thermostability from the family A and the family B among 6 types of DNA polymerases, analyzed the amplification performance characteristics of each enzyme, and selected chimeric candidates. Based on polymerase structure analysis, sequence analysis, and taking the requirement on the amplification fidelity into consideration, novel chimeric DNA polymerases with potential functions were screened through different chimerism of amino acid sequences of various domains of 2, 3, 4 or 5 types of enzymes, containing the amino acid sequences of corresponding domains of the following 7 DNA polymerases. These DNA polymerases are all DNA polymerases of the family B of archaea, derived from *Pyrococcus furiosus* (Pfu), *Thermococcus kodacaraensis* (KOD), *Pyrococcus woesei* (Pwo), *Thermococcus gorgonarius* (Tgo), *Pyrococcus abyssi* (Pab), *Pyrococcus* species GB-D (Deep vent), and *Thermococcus* sp. 9°N-7 (9°N), respectively. The above-mentioned 7 types of DNA polymerases each having 5 domains provide different combinations of domains. That is, there are 7 candidates for each domain of the chimeric polymerase, and accordingly, a total of $(5^7-7)$ chimeric forms for the possible chimeric polymerases.

In order to further narrow the above chimeric library, the performances thereof are analyzed as follow for optimization analysis. The performance characteristics of the above 7 types of DNA polymerases were compared and analyzed. For example, the DNA polymerases, Pfu and Pab, have better fidelity performance than other enzymes. Therefore, the chimeric combinations whose exonucleolytic domains are the corresponding nucleoside sequence of these two DNA polymerases are preferred.

Similarly, the candidate sequences, which are suitable as the palm, finger, thumb and N-end domains, are screened based on the research and analysis of the amplification performance and thermal stability of the respective enzymes, in order to further reduce the chimeric combinations. Through the above screening, the corresponding nucleotide sequences were obtained based on the amino acid sequences of the candidate chimeric polymerases, and constructed into expression vectors. The expression bacteria are induced to express the candidate chimeric polymerases, and the expressed candidate chimeric polymerases are then purified. The expression performance, fidelity, thermal stability and synthesis capability of the chimeric enzymes were compared with each other, in order to select the optimal chimeric DNA polymerase of the present disclosure. The chimeric DNA polymerase having the structure as illustrated in FIG. 1 has high processivity, high elongation rate, thermal stability, strong resistance to salts, and high fidelity, which can meet the requirements of DNA amplification, synthesis, detection, and sequencing, etc., thereby having a broad application prospect.

Amino acid sequence of Pab DNA polymerase (SEQ ID NO: 3):
MIIDADYITEDGKPIIRIFKKEKGEFKVEYDRTFRPYIYALLKDDSAIDEVKKITAERHG

KIVRITEVEKVQKKFLGRPIEVWKLYLEHPQDVPAIREKIREHPAVVDIFEYDIPFAKRY

LIDKGLTPMEGNEELTFLAVDIETLYHEGEEFGKGPIIMISYADEEGAKVITWKSID

LPYVEVVSSEREMIKRLVKVIREKDPDVIITYNGDNFDFPYLLKRAEKLGIKLPL

GRDNSEPKMQRMGDSLAVEIKGRIHFDLFPVIRRTINLPTYTLEAVYEAIFGKSK

EKVYAHEIAEAWETGKGLERVAKYSMEDAKVTFELGKEFFPMEAQLARLVGQP

VWDVSRSSTGNLVEWFLLRKAYERNELAPNKPDEREYERRLRESYEGGYVKEPEKG

LWEGIVSLDFRSLYPSIIITHNVSPDTLNRENCKEYDVAPQVGHRFCKDFPG<u>FIPSLLGN</u>

<u>LLEERQKIKKRMKESKDPVEKKLLDYRQRAIKILANSYYGYYGY</u>AKARWYCKE

CAESVTAWGRQYIDLVRRELESRGFKVLYIDTDGLYATIPGAKHEEIKEKALKFVEYIN

SKLPGLLELEYEGFYARGFFVTKKKYALIDEEGKIVTRGLEIVRRDWSEIAKETQAKV

LEAILKHGNVDEAVKIVKEVTEKLSKYEIPPEKLVIYEQITRPLSEYKAIGPHVAVAKRL

AAKGVKVKPGMVIGYIVLRGDGPISKRAIAIEEFDPKKHKYDAEYYIENQVLPAVERI

LRAFGYRKEDLKYQKTKQVGLGAWLKF

Amino acid sequence of Pfu DNA polymerase (SEQ ID NO: 4):
MILDVDYITEEGKPVIRLFKKENGKFKIEHDRTFRPYIYALLRDDSKIEEVKKITGERH

GKIVRIVDVEKVEKKFLGKPITVWKLYLEHPQDVPTLREKVREHPAVVDIFEYDIPFA

KRYLIDKGLIPMEGEEELKILAFDIETLYHEGEEFGKGPIIMISYADENEARVITWKNID

LPYVESVSTEKEMIKRFLRIIREKDPDIIVTYNGDSFDFPYLAKRAEKLGIKLTIGRDGS

EPKMQRIGDMTAVEVKGRIHFDLYHVIRTTINLPTYTLEAVYEAIFGKPKEKVYADEI

AKAWESGENLERVAKYSMEDAKATYELGKEFLPMEIQLSRLVGQPLWDVSRSSTGN

LVEWFLLRKAYERNEVAPNKPSEEEYQRRLRESYTGGFVKEPEKGLWENIVYLD

YKSLYPSIIITHNVSPDTLNLEGCKNYDIAPQVGHKFCKDIPGFIPSLLGHLLEER

QKIKTKMKETQDPIEKILLDYRQKAIKLLANSFYGYYGYAKARWYCKECAESV

TAWGRKYIELVWKELEEKFGFKVLYIDTDGLYATIPGGESEEIKKKALEFVKYI

NSKLPGLLELEYEGFYKRGFFVTKKRYAVIDEEGKVITRGLEIVRRDWSEIAKETQ

ARVLETILKHGDVEEAVRIVKEVIQKLANYEIPPEKLAIYEQITRPLHEYKAIGPHVAV

AKKLAAKGVKIKPGMVIGYIVLRGDGPISNRAILAEEYDPKKHKYDAEYYIENQVLP

AVLRILEGFGYRKEDLRYQKTRQVGLTSWLNIKKS

Amino acid sequence of KOD DNA polymerase (SEQ ID NO: 5):
MILDTDYITEDGKPVIRIFKKENGEFKIEYDRTFEPYFYALLKDDSAIEEVKKITA

ERHGTVVTVKRVEKVQKKFLGRPVEVWKLYFTHPQDVPAIRDKIREHPAVIDIY

EYDIPFAKRYLIDKGLVPMEGDEELKMLAFDIETLYHEGEEFAEGPILMISYADEEGA

RVITWKNVDLPYVDVVSTEREMIKRFLRVVKEKDPDVLITYNGDNFDFAYLKKRCEK

LGINFALGRDGSEPKIQRMGDRFAVEVKGRIHFDLYPVIRRTINLPTYTLEAVYEAVFG

QPKEKVYAEEITTAWETGENLERVARYSMEDAKVTYELGKEFLPMEAQLSRLI<u>GQSL</u>

<u>WDVSRSSTGNLVEWFLLRKAYERNELAPNKP</u>DEKELARRRQSYEGGYVKEPERGLW

ENIVYLDFRSLYPSIIITHNVSPDTLNREGCKEYDVAPQVGHRFCKDFPGFIPSLLGDLL

EERQKIKKKMKATIDPIERKLLDYRQRAIKILANSYYGYYGYARARWYCKECAESVT

AWGREYITMTIKEIEEKYGFKVIYSDTDGFFATIPGADAETVKKKAMEFLKYINAKLP

GALELEYEGFYKRGFFVTKKKYAVIDEEGKITTRGLEIVRRDWSEIAKETQARVLE

-continued
ALLKDGDVEKAVRIVKEVTEKLSKYEVPPEKLVIHEQITRDLKDYKATGPHVAVA

KRLAARGVKIRPGTVISYIVLKGSGRIGDRAIPFDEFDPTKHKYDAEYYIENQVL

PAVERILRAFGYRKEDLRYQKTRQVGLSAWLKPKGT

According to an embodiment of the present disclosure, the first peptide fragment has at least 80% homology to an amino acid sequence of sites 1 to 130 of the KOD DNA polymerase. The amino acid sequence of sites 1 to 130 of the KOD DNA polymerase is a first gray-marked sequence fragment in the sequence set forth as SEQ ID NO: 5, i.e., a partial sequence in the N-end domain of the KOD DNA polymerase.

According to an embodiment of the present disclosure, the second peptide fragment has at least 80% homology to an amino acid sequence of sites 131 to 337 of the Pab DNA polymerase. The amino acid sequence of sites 131 to 337 of the Pab DNA polymerase is a first gray-marked sequence fragment in the sequence set forth as SEQ ID NO: 3, i.e., a partial sequence in the exonucleolytic domain of the Pab DNA polymerase.

According to an embodiment of the present disclosure, the third peptide fragment has at least 80% homology to an amino acid sequence of sites 338 to 373 of the KOD DNA polymerase. The amino acid sequence of sites 338 to 373 of the KOD DNA polymerase is a second gray-marked sequence fragment in a sequence set forth as SEQ ID NO: 5, i.e., a partial sequence in the N-end domain of the KOD DNA polymerase.

According to an embodiment of the present disclosure, the fourth peptide fragment has at least 80% homology to an amino acid sequence of sites 374 to 448 of the Pfu DNA polymerase. The amino acid sequence of sites 374 to 448 of the Pfu DNA polymerase is a first gray-marked sequence fragment in the sequence set forth as SEQ ID NO: 4, i.e., a partial sequence in the palm domain of the Pfu DNA polymerase.

According to an embodiment of the present disclosure, the fifth peptide fragment has at least 80% homology to an amino acid sequence of sites 449 to 500 of the Pab DNA polymerase. The amino acid sequence of sites 449 to 500 of the Pab DNA polymerase is a second gray-marked sequence fragment in the sequence set forth as SEQ ID NO: 3, i.e., a partial sequence in the finger domain of the Pab DNA polymerase.

According to an embodiment of the present disclosure, the sixth peptide fragment has at least 80% homology to an amino acid sequence of sites 501 to 591 of the Pfu DNA polymerase. The amino acid sequence of sites 501 to 591 of the Pfu DNA polymerase is a second gray-marked sequence fragment in the sequence set forth as SEQ ID NO: 4, i.e., a partial sequence in the palm domain of the Pfu DNA polymerase.

According to an embodiment of the present disclosure, the seventh peptide fragment has at least 80% homology to an amino acid sequence of sites 591 to 774 of the KOD DNA polymerase. The amino acid sequence of sites 591 to 774 of the KOD DNA polymerase is a third gray-marked sequence in the sequence set forth as SEQ ID NO: 5, i.e., a partial sequence in the thumb domain of the KOD DNA polymerase.

As a result, the obtained chimeric DNA polymerases have the properties such as high processivity, high elongation rate, thermal stability, strong resistance to salts, and high fidelity, and thus they can meet the requirements of DNA amplification, synthesis, detection, sequencing, etc., thereby having a broad application prospect.

According to an embodiment of the present disclosure, the chimeric DNA polymerase has the amino acid sequence set forth as SEQ ID NO: 1. In this way, the chimeric DNA polymerase according to the embodiment of the present disclosure has the properties such as high processivity, high elongation rate, thermal stability, strong resistance to salts, and high fidelity, and it can meet the requirements of DNA amplification, synthesis, detection, sequencing, etc., thereby having a broad application prospect.

(SEQ ID NO: 1)
MILDTDYITEDGKPVIRIFKKENGEFKIEYDRTFEPYFYALLKDDSAIE

EVKKITAERHGTVVTVKRVEKVQKKFLGRPVEVWKLYFTHPQDVPAIRD

KIREHPAVIDIYEYDIPFAKRYLIDKGLVPMEGNEELTFLAVDIETLYH

EGEEFGKGPIIMISYADEEGAKVITWKSIDLPYVEVVSSEREMIKRLVK

VIREKDPDVIITYNGDNFDFPYLLKRAEKLGIKLPLGRDNSEPKMQRMG

DSLAVEIKGRIHFDLFPVIRRTINLPTYTLEAVYEAIFGKSKEKVYAHE

IAEAWETGKGLERVAKYSMEDAKVTFELGKEFFPMEAQLARLVGQSLWD

VSRSSTGNLVEWFLLRKAYERNELAPNKPDEEEYQRRLRESYTGGFVKE

PEKGLWENIVYLDYKSLYPSIIITHNVSPDTLNLEGCKNYDIAPQVGHK

FCKDIPGFIPSLLGNLLEERQKIKKRMKESKDPVEKKLLDYRQRAIKIL

ANSYYGYYGYAKARWYCKECAESVTAWGRKYIELVWKELEEKFGFKVLY

IDTDGLYATIPGGESEEIKKKALEFVKYINSKLPGLLELEYEGFYKRGF

FVTKKKYAVIDEEGKITTRGLEIVRRDWSEIAKETQARVLEALLKDGDV

EKAVRIVKEVTEKLSKYEVPPEKLVIHEQITRDLKDYKATGPHVAVAKR

LAARGVKIRPGTVISYIVLKGSGRIGDRAIPFDEFDPTKHKYDAEYYIE

NQVLPAVERILRAFGYRKEDLRYQKTRQVGLSAWLKPKGT

Isolated Nucleic Acid

In another aspect of the present disclosure, the present disclosure provides an isolated nucleic acid. According to an embodiment of the present disclosure, the isolated nucleic acid encodes the aforementioned chimeric DNA polymerase. Thus, the isolated nucleic acid according to the embodiment of the present disclosure can be used to encode the chimeric DNA polymerase having the properties such as high processivity, high elongation rate, thermal stability, strong resistance to salts, and high fidelity, which can meet the requirements of DNA amplification, synthesis, detection, sequencing, etc., thereby having a broad application prospect.

According to an embodiment of the present disclosure, a nucleic acid encoding the first peptide fragment has at least 80% homology to a nucleotide sequence of sites 1 to 390 of the KOD DNA polymerase. The sequence of sites 1 to 390 of the nucleotide sequence encoding the KOD DNA polymerase is a first gray-marked sequence fragment in a sequence set forth as SEQ ID NO: 8, i.e., a partial sequence encoding the N-end domain of the encoding KOD DNA polymerase.

According to an embodiment of the present disclosure, a nucleic acid encoding the second peptide fragment has at least 80% homology to a nucleotide sequence of sites 391 to 1011 of the Pab DNA polymerase. The sequence of sites 391 to 1011 of a nucleotide sequence encoding the Pab DNA polymerase is a first gray-marked sequence fragment in a sequence set forth as SEQ ID NO: 6, i.e., a partial sequence encoding the exonucleolytic domain of the Pab DNA polymerase.

According to an embodiment of the present disclosure, a nucleic acid encoding the third peptide fragment has at least 80% homology to a nucleotide sequence at sites 1012 to 1119 of the KOD DNA polymerase. The sequence of sites 1012 to 1119 of the nucleotide sequence encoding the KOD DNA polymerase is a second gray-marked sequence fragment in the sequence set forth as SEQ ID NO: 8, i.e., a partial sequence encoding the N-end domain of the encoding KOD DNA polymerase.

According to an embodiment of the present disclosure, a nucleic acid encoding the fourth peptide fragment has at least 80% homology to a nucleotide sequence of sites 1120 to 1344 of the Pfu DNA polymerase. The sequence of sites 1120 to 1344 of a nucleotide sequence encoding the Pfu DNA polymerase is a first gray-marked sequence fragment in a sequence set forth as SEQ ID NO: 7, i.e., a partial sequence encoding the palm domain of the Pfu DNA polymerase.

According to an embodiment of the present disclosure, a nucleic acid encoding the fifth peptide fragment has at least 80% homology to a nucleotide sequence at sites 1345 to 1500 of the Pab DNA polymerase. The sequence of sites 1345 to 1500 of the nucleotide sequence encoding the Pab DNA polymerase is a second gray-marked sequence in the sequence set forth as SEQ ID NO: 6, i.e., a partial sequence encoding the finger domain of the Pab DNA polymerase.

According to an embodiment of the present disclosure, a nucleic acid encoding the sixth peptide fragment has at least 80% homology to a nucleotide sequence of sites 1501 to 1773 of the Pfu DNA polymerase. The sequence of sites 1501 to 1773 of the nucleotide sequence encoding the Pfu DNA polymerase is a second gray-marked sequence in the sequence set forth as SEQ ID NO: 7, i.e., a partial sequence encoding the palm domain of the Pfu DNA polymerase.

According to an embodiment of the present disclosure, a nucleic acid encoding the seventh peptide fragment has at least 80% homology to a nucleotide sequence of sites 1771 to 2325 of the KOD DNA polymerase. The sequence of sites 1771 to 2325 of the nucleotide sequence encoding the KOD DNA polymerase is a third gray-marked sequence in the sequence set forth as SEQ ID NO: 8, i.e., a partial sequence encoding the thumb domain of KOD DNA polymerase.

As a result, the obtained chimeric DNA polymerase has the properties such as high processivity, high elongation rate, thermal stability, strong resistance to salts, and high fidelity, and thus it can meet the requirements of DNA amplification, synthesis, detection, sequencing, etc., thereby having a broad application prospect.

According to an embodiment of the present disclosure, the isolated nucleic acid has a nucleotide sequence set forth as SEQ ID NO:2.

(SEQ ID NO: 2)

```
ATGATTCTGGACACCGATTACATCACCGAAGATGGCAAGCCAGTTATCCGCATTTT

CAAAAAAGAGAATGGTGAATTCAAGATCGAATATGATCGTACCTTCGAGCCGTACT

TCTATGCTCTGCTGAAAGACGATAGCGCGATTGAGGAGGTCAAGAAAATCACCGC

GGAGCGTCACGGTACGGTTGTTACCGTGAAACGCGTGGAGAAAGTCCAGAAGAA

ATTTCTGGGTCGCCCGGTTGAAGTGTGGAAGCTGTACTTTACGCATCCGCAAGATG

TTCCGGCGATTCGCGATAAGATTCGTGAGCACCCGGCAGTCATTGACATCTACGAG

TATGACATTCCGTTCGCCAAGCGTTATCTGATCGATAAGGGTCTGGTCCCGATGGA

GGGGAACGAGGAGCTAACGTTTCTAGCCGTTGATATAGAAACATTGTACCATGAA

GGAGAGGAGTTCGGGAAAGGGCCAATAATAATGATCAGCTACGCCGACGAGGAA

GGGGCCAAGGTGATAACTTGGAAGAGCATAGACTTACCTTACGTTGAAGTGGTTT

CGAGCGAGAGGGAGATGATAAAGAGGCTCGTGAAGGTAATTAGAGAGAAAGATC

CCGACGTGATAATAACGTACAATGGTGATAATTTCGACTTTCCGTACCTCTTAAAGA

GGGCTGAAAAGCTCGGAATAAAGCTCCCCCTTGGAAGGGACAATAGCGAGCCGA

AAATGCAGAGGATGGGGGATTCATTAGCCGTAGAGATAAAGGGCAGAATACACTT

CGATTTATTCCCCGTCATAAGAAGAACGATCAACCTTCCAACATACACCCTCGAAG

CGGTTTATGAGGCTATATTTGGAAAGTCTAAGGAGAAAGTCTATGCCCATGAGATA

GCTGAGGCCTGGGAAACCGGGAAAGGGCTAGAGAGGGTAGCTAAGTATTCAATG

GAAGATGCGAAGGTAACCTTTGAGCTCGGAAAGGAGTTCTTCCCGATGGAAGCCC

AGCTAGCTAGGCTCGTTGGCCAAAGCCTGTGGGACGTTAGCCGCAGCAGCACCGG

TAACTTAGTTGAATGGTTCTTGCTGCGTAAGGCATACGAACGCAATGAGCTGGCGC
```

CGAACAAACCGGACGAAGAGGAGTATCAAAGAAGGCTCAGGGAGAGCTACACA

GGTGGATTCGTTAAAGAGCCAGAAAAGGGGTTGTGGGAAAACATAGTATACCTAG

ATTACAAATCACTATATCCCTCGATTATAATTACCCACAATGTTTCTCCCGATACTCT

AAATCTTGAGGGATGCAAGAACTATGATATCGCTCCTCAAGTAGGCCACAAGTTCT

GCAAGGACATCCCTGGTTTCATACCAAGCTTACTGGGTAACCTACTGGAGGAGAG

ACAAAAGATAAAAAAGAGAATGAAAGAAAGTAAAGATCCCGTCGAGAAGAAACT

CCTTGATTACAGACAGAGAGCTATAAAAATACTTGCAAACAGCTATTATGGCTATTA

TGGATATGCAAAAGCAAGATGGTACTGTAAGGAGTGTGCTGAGAGCGTTACTGCC

TGGGGAAGAAAGTACATCGAGTTAGTATGGAAGGAGCTCGAAGAAAAGTTTGGAT

TTAAAGTCCTCTACATTGACACTGATGGTCTCTATGCAACTATCCCAGGAGGAGAA

AGTGAGGAAATAAAGAAAAAGGCTCTAGAATTTGTAAAATACATAAATTCAAAGC

TCCCTGGACTGCTAGAGCTTGAATATGAAGGGTTTTATAAGAGGGGATTCTTCGTT

ACGAAAAAGAAATACGCTGTTATTGATGAAGAGGGCAAGATCACGACCCGTGGCC

TGGAAATTGTGCGCCGTGATTGGAGCGAAATTGCAAAAGAAACGCAAGCGCGTG

TGCTGGAAGCGCTGCTGAAGGACGGCGACGTCGAAAAAGCTGTGCGTATTGTTAA

AGAGGTCACCGAGAAGCTGAGCAAATACGAGGTCCCGCCAGAGAAATTGGTGAT

TCACGAACAGATTACGCGTGACCTGAAAGACTATAAGGCCACCGGTCCGCATGTC

GCAGTGGCGAAGCGCCTGGCGGCTCGCGGTGTGAAGATCCGTCCGGGTACCGTC

ATTAGCTATATCGTGCTGAAGGGCAGCGGTCGTATCGGCGACCGTGCGATTCCGTT

CGACGAATTTGATCCGACCAAACACAAATATGATGCGGAATACTATATTGAGAACC

AAGTGCTGCCAGCCGTTGAGCGTATTCTGCGCGCCTTCGGTTACCGCAAGGAAGA

TCTGCGTTACCAGAAAACTCGTCAGGTCGGTCTGTCCGCATGGCTGAAACCGAAG

GGCACCTGA

Nucleotide sequence of Pab DNA polymerase (SEQ ID NO: 6):
ATGATAATCGATGCTGATTACATAACGGAAGATGGCAAGCCGATAATAAGGATATTC

AAAAAGGAAAAGGGAGAGTTTAAGGTAGAATACGATAGGACGTTTAGACCCTACA

TTTATGCTCTTTTAAAGGATGATTCGGCCATAGATGAGGTTAAGAAGATAACCGCC

GAGAGGCACGGAAAGATAGTCAGGATAACCGAGGTTGAGAAAGTCCAGAAGAAA

TTCCTAGGAAGGCCAATAGAAGTCTGGAAGCTCTATCTTGAGCATCCCCAGGATGT

TCCAGCCATAAGAGAGAAGATAAGGGAACATCCAGCTGTAGTTGATATATTTGAAT

ACGACATACCCTTTGCGAAGCGCTACCTCATAGACAAGGGATTGACTCCAATGGA

GGGGAACGAGGAGCTAACGTTTCTAGCCGTTGATATAGAAACATTGTACCAT

GAAGGAGAGGAGTTCGGGAAAGGGCCAATAATAATGATCAGCTACGCCGAC

GAGGAAGGGGCCAAGGTGATAACTTGGAAGAGCATAGACTTACCTTACGTTG

AAGTGGTTTCGAGCGAGAGGGAGATGATAAAGAGGCTCGTGAAGGTAATTA

GAGAGAAAGATCCCGACGTGATAATAACGTACAATGGTGATAATTTCGACTTT

CCGTACCTCTTAAAGAGGGCTGAAAAGCTCGGAATAAAGCTCCCCCTTGGAA

GGGACAATAGCGAGCCGAAAATGCAGAGGATGGGGGATTCATTAGCCGTAGA

GATAAAGGGCAGAATACACTTCGATTTATTCCCCGTCATAAGAAGAACGATCA

ACCTTCCAACATACACCCTCGAAGCGGTTTATGAGGCTATATTTGGAAAGTCT

AAGGAGAAAGTCTATGCCCATGAGATAGCTGAGGCCTGGGAAACCGGGAAA

GGGCTAGAGAGGGTAGCTAAGTATTCAATGGAAGATGCGAAGGTAACCTTTG

AGCTCGGAAAGGAGTTCTTCCCGATGGAAGCCCAGCTAGCTAGGCTCGTTGG

CCAGCCAGTTTGGGACGTTTCAAGGTCGAGCACCGGAAACCTCGTTGAGTGGTTT

CTCCTTAGGAAGGCCTACGAGAGAAATGAGCTCGCGCCCAATAAACCGGACGAG

AGGGAATACGAGAGAAGGCTAAGAGAGAGCTATGAAGGGGGTTACGTTAAGGAG

CCAGAGAAGGGATTGTGGGAAGGGATAGTCAGCTTAGACTTTAGGTCCCTATATCC

CTCTATAATTATAACTCACAACGTCTCACCAGACACTTTGAATAGAGAAAATTGCA

AGGAATATGACGTTGCCCCCCAAGTGGGGCACAGATTCTGCAAGGATTTCCCAGG

ATTCATACCAAGCTTACTGGGTAACCTACTGGAGGAGAGACAAAGATAAAA

AAGAGAATGAAAGAAAGTAAAGATCCCGTCGAGAAGAAACTCCTTGATTACA

GACAGAGAGCTATAAAAATACTTGCAAACAGCTATTATGGCTATTATGGATATG

CAAAGGCCAGATGGTACTGTAAAGAGTGTGCAGAGAGCGTAACCGCATGGGGAA

GGCAGTACATAGACCTGGTTAGGAGGGAACTTGAGAGCAGAGGATTTAAAGTTCT

CTACATAGACACAGATGGCCTCTACGCAACGATTCCTGGAGCCAAGCATGAGGAA

ATAAAAGAGAAGGCATTGAAGTTCGTCGAGTACATAAACTCCAAGTTACCTGGGC

TTCTTGAATTGGAATACGAAGGTTTCTACGCGAGAGGGTTCTTCGTGACGAAGAA

AAAGTACGCACTAATCGACGAGGAAGGAAAGATAGTTACGAGGGGGCTCGAAAT

AGTAAGGAGAGATTGGAGTGAAATAGCAAAGGAGACCCAGGCCAAGGTTCTTGA

GGCAATACTCAAGCACGGTAACGTTGATGAGGCCGTAAAAATAGTAAAGGAGGTT

ACAGAAAAACTCAGTAAATATGAAATACCACCCGAAAAGCTTGTAATTTATGAGCA

GATAACGAGGCCTCTGAGCGAGTATAAAGCGATAGGCCCTCACGTTGCAGTAGCT

AAAAGGCTCGCAGCGAAGGGAGTAAAAGTTAAGCCAGGGATGGTTATCGGTTAC

ATAGTTTTGAGGGGAGACGGGCCAATAAGCAAGAGGGCCATAGCTATAGAGGAGT

TCGATCCCAAAAAGCATAAGTACGATGCCGAATACTACATAGAGAACCAAGTTCTG

CCAGCGGTGGAGAGGATATTGAGAGCATTTGGTTATCGCAAGGAGGATTTGAAGT

ATCAAAAAACTAAACAAGTGGGCCTTGGAGCATGGCTTAAGTTCTGA

Nucleotide sequence of Pfu DNA polymerase (SEQ ID NO: 7):
ATGATTTTAGATGTGGATTACATAACTGAAGAAGGAAAACCTGTTATTAG

GCTATTCAAAAAAGAGAACGGAAAATTTAAGATAGAGCATGATAGAACTTTTAGA

CCATACATTTACGCTCTTCTCAGGGATGATTCAAAGATTGAAGAAGTTAAGAAAAT

AACGGGGGAAAGGCATGGAAAGATTGTGAGAATTGTTGATGTAGAGAAGGTTGA

GAAAAGTTTCTCGGCAAGCCTATTACCGTGTGGAAACTTTATTTGGAACATCCCC

AAGATGTTCCCACTTTAAGAGAAAAAGTTAGAGAACATCCAGCAGTTGTGGACAT

CTTCGAATACGATATTCCATTTGCAAAGAGATACCTCATCGACAAAGGCCTAATACC

AATGGAGGGGGAAGAAGAGCTAAAGATTCTTGCCTTCGATATAGAAACCCTCTATC

ACGAAGGAGAAGAGTTTGGAAAAGGCCCCAATTATAATGATTAGTTATGCAGATGA

AAATGAAGCAAGGGTGATTACTTGGAAAAAACATAGATCTTCCATACGTTGAGTCA

GTATCAACCGAGAAAGAGATGATAAAGAGATTTCTCAGGATTATCAGGGAGAAGG

ATCCTGACATTATAGTTACTTATAATGGAGACTCATTCGACTTCCCATATTTAGCGAA

AAGGGCAGAAAAACTTGGGATTAAATTAACCATTGGAAGAGATGGAAGCGAGCC

CAAGATGCAGAGAATAGGCGATATGACGGCTGTAGAAGTCAAGGGAAGAATACAT

-continued

TTCGACTTGTATCATGTAATAAGGACAACAATAAATCTCCCAACATACACACTAGA

GGCTGTATATGAAGCAATTTTTGGAAAGCCAAAGGAGAAGGTATACGCCGACGAG

ATAGCAAAAGCCTGGGAAAGTGGAGAGAACCTTGAGAGAGTTGCCAAATACTCG

ATGGAAGATGCAAAGGCAACTTATGAACTCGGGAAAGAATTCCTTCCAATGGAAA

TTCAGCTTTCAAGATTAGTTGGACAACCTTTATGGGATGTTTCAAGGTCAAGCACA

GGGAACCTTGTAGAGTGGTTCTTACTTAGGAAAGCCTACGAAAGAAACGAAGTAG

CTCCAAACAAGCCAAGTGAAGAGGAGTATCAAAGAAGGCTCAGGGAGAGCTA

CACAGGTGGATTCGTTAAAGAGCCAGAAAAGGGGTTGTGGGAAAACATAGTA

TACCTAGATTACAAATCACTATATCCCTCGATTATAATTACCCACAATGTTTCT

CCCGATACTCTAAATCTTGAGGGATGCAAGAACTATGATATCGCTCCTCAAGT

AGGCCACAAGTTCTGCAAGGACATCCCTGGTTTTATACCAAGTCTCTTGGGACA

TTTGTTAGAGGAAAGACAAAAGATTAAGACAAAAATGAAGGAAACTCAAGATCC

TATAGAAAAAATACTCCTTGACTATAGACAAAAAGCGATAAAACTCTTAGCAAATT

CTTTCTACGGATATTATGGCTATGCAAAAGCAAGATGGTACTGTAAGGAGTGTG

CTGAGAGCGTTACTGCCTGGGGAAGAAAGTACATCGAGTTAGTATGGAAGGA

GCTCGAAGAAAAGTTTGGATTTAAAGTCCTCTACATTGACACTGATGGTCTCT

ATGCAACTATCCCAGGAGGAGAAAGTGAGGAAATAAAGAAAAAGGCTCTAGA

ATTTGTAAAATACATAAATTCAAAGCTCCCTGGACTGCTAGAGCTTGAATATG

AAGGGTTTTATAAGAGGGGATTCTTCGTTACGAAGAAGAGGTATGCAGTAATA

GATGAAGAAGGAAAAGTCATTACTCGTGGTTTAGAGATAGTTAGGAGAGATTGGA

GTGAAATTGCAAAAGAAACTCAAGCTAGAGTTTTGGAGACAATACTAAAACACGG

AGATGTTGAAGAAGCTGTGAGAATAGTAAAAGAAGTAATACAAAAGCTTGCCAAT

TATGAAATTCCACCAGAGAAGCTCGCAATATATGAGCAGATAACAAGACCATTACA

TGAGTATAAGGCGATAGGTCCTCACGTAGCTGTTGCAAAGAAACTAGCTGCTAAA

GGAGTTAAAATAAAGCCAGGAATGGTAATTGGATACATAGTACTTAGAGGCGATGG

TCCAATTAGCAATAGGGCAATTCTAGCTGAGGAATACGATCCCAAAAAGCACAAG

TATGACGCAGAATATTACATTGAGAACCAGGTTCTTCCAGCGGTACTTAGGATATTG

GAGGGATTTGGATACAGAAAGGAAGACCTCAGATACCAAAAGACAAGACAAGTC

GGCCTAACTTCCTGGCTTAACATTAAAAAATCCTGA

Nucleotide sequence of KOD DNA polymerase (SEQ ID NO: 8):
ATGATTCTGGACACCGATTACATCACCGAAGATGGCAAGCCAGTTA

TCCGCATTTTCAAAAAAGAGAATGGTGAATTCAAGATCGAATATGATCGTACC

TTCGAGCCGTACTTCTATGCTCTGCTGAAAGACGATAGCGCGATTGAGGAGG

TCAAGAAAATCACCGCGGAGCGTCACGGTACGGTTGTTACCGTGAAACGCG

TGGAGAAAGTCCAGAAGAAATTTCTGGGTCGCCCGGTTGAAGTGTGGAAGC

TGTACTTTACGCATCCGCAAGATGTTCCGGCGATTCGCGATAAGATTCGTGA

GCACCCGGCAGTCATTGACATCTACGAGTATGACATTCCGTTCGCCAAGCGT

TATCTGATCGATAAGGGTCTGGTCCCGATGGAGGGTGACGAAGAACTGAAGAT

GCTGGCGTTCGACATCGAAACTCTGTACCACGAGGGTGAAGAGTTTGCCGAGGGT

CCGATCTTGATGATTTCCTACGCGGACGAAGAGGGCGCACGTGTTATCACGTGGA

AAAATGTTGATCTGCCGTATGTTGACGTCGTAAGCACCGAGCGTGAGATGATCAA

-continued

ACGTTTTCTGCGCGTTGTTAAAGAAAAAGATCCTGACGTGCTGATCACCTACAAC

GGTGACAATTTCGATTTCGCGTACCTGAAGAAACGTTGCGAAAAACTGGGTATTA

ACTTCGCGCTGGGTCGCGATGGCTCTGAACCGAAGATCCAGCGCATGGGTGATCG

TTTTGCGGTCGAGGTGAAGGGTCGCATTCATTTCGACCTGTACCCGGTGATTCGTC

GTACCATCAACTTGCCGACTTACACCCTGGAAGCCGTCTATGAAGCTGTATTTGGT

CAACCGAAAGAAAAAGTGTACGCTGAGGAAATTACGACGGCGTGGGAAACCGGT

GAGAACCTGGAGCGCGTTGCACGTTATTCTATGGAGGACGCGAAAGTTACCTACG

AACTGGGTAAAGAGTTCCTGCCGATGGAGGCCCAACTGTCCCGTCTGATCGGCCA

AAGCCTGTGGGACGTTAGCCGCAGCAGCACCGGTAACTTAGTTGAATGGTTC

TTGCTGCGTAAGGCATACGAACGCAATGAGCTGGCGCCGAACAAACCGGAC

GAGAAAGAATTGGCGCGTCGCCGCCAGAGCTATGAGGGTGGTTATGTCAAAGAAC

CGGAGCGCGGCTTGTGGGAGAACATCGTCTATTTGGATTTTCGTAGCCTGTACCCG

AGCATCATTATCACGCATAATGTGAGCCCGGATACGTTGAATCGTGAGGGCTGTAA

GGAATACGACGTGGCGCCTCAGGTTGGCCACCGTTTCTGCAAGGACTTTCCGGGC

TTTATCCCGAGCCTGCTGGGTGATTTGCTGGAGGAACGTCAGAAAATCAAGAAGA

AGATGAAAGCAACCATTGATCCGATCGAGCGCAAATTACTGGACTACCGTCAACG

TGCCATCAAGATCCTGGCGAATTCGTATTATGGTTACTATGGCTACGCGCGTGCGCG

CTGGTATTGCAAAGAGTGTGCCGAGAGCGTGACCGCTTGGGGTCGTGAGTACATT

ACCATGACGATCAAAGAGATTGAAGAGAAATACGGCTTTAAGGTTATCTATAGCGA

CACCGACGGTTTCTTTGCAACTATCCCTGGCGCAGACGCAGAAACCGTTAAGAAA

AAGGCAATGGAGTTTCTGAAGTATATCAACGCGAAGTTGCCAGGCGCCCTGGAAC

TGGAGTACGAGGGCTTCTACAAGCGTGGCTTTTTCGTGACGAAAAAGAAATACG

CTGTTATTGATGAAGAGGGCAAGATCACGACCCGTGGCCTGGAAATTGTGCG

CCGTGATTGGAGCGAAATTGCAAAAGAAACGCAAGCGCGTGTGCTGGAAGC

GCTGCTGAAGGACGGCGACGTCGAAAAAGCTGTGCGTATTGTTAAAGAGGT

CACCGAGAAGCTGAGCAAATACGAGGTCCCGCCAGAGAAATTGGTGATTCAC

GAACAGATTACGCGTGACCTGAAAGACTATAAGGCCACCGGTCCGCATGTCG

CAGTGGCGAAGCGCCTGGCGGCTCGCGGTGTGAAGATCCGTCCGGGTACCG

TCATTAGCTATATCGTGCTGAAGGGCAGCGGTCGTATCGGCGACCGTGCGAT

TCCGTTCGACGAATTTGATCCGACCAAACACAAATATGATGCGGAATACTATA

TTGAGAACCAAGTGCTGCCAGCCGTTGAGCGTATTCTGCGCGCCTTCGGTTA

CCGCAAGGAAGATCTGCGTTACCAGAAAACTCGTCAGGTCGGTCTGTCCGC

ATGGCTGAAACCGAAGGGCACCTGA

It can be understood by those skilled in the art that the isolated nucleic acid has the similar features and advantages of the chimeric DNA polymerases as described above, which will not be repeated herein.

Construct

In yet another aspect of the present disclosure, the present disclosure provides a construct. According to an embodiment of the present disclosure, the construct contains the isolated nucleic acid as described above. Thus, the construct according to the embodiment of the present disclosure can express the chimeric DNA polymerase having the properties such as high processivity, high elongation rate, thermal stability, strong resistance to salts, and high fidelity, which can meet the requirements of DNA amplification, synthesis, detection, sequencing, etc., thereby having a broad application prospect.

It will be understood by those skilled in the art that the construct has the similar features and advantages of the isolated nucleic acid as described above, which will not be repeated herein.

Recombinant Cell or Recombinant Microorganism

In yet another aspect of the present disclosure, the present disclosure provides a recombinant cell or recombinant microorganism. According to an embodiment of the present disclosure, the recombinant cell or recombinant microorganism contains the isolated nucleic acid as described above. Thus, the recombinant cell or recombinant microorganism according to the embodiments of the present disclosure can express the chimeric DNA polymerase having the properties such as high processivity, high elongation rate, thermal stability, strong resistance to salts, and high fidelity, which can meet the requirements of DNA amplification, synthesis, detection, sequencing, etc., thereby having a broad application prospect.

Those skilled in the art can understand that the recombinant cell or recombinant microorganism has the similar features and advantages of the isolated nucleic acid as described above, which will not be repeated herein.

Method for Obtaining Chimeric DNA Polymerase

In yet another aspect of the present disclosure, the present disclosure provides a method for obtaining the aforementioned chimeric DNA polymerase. According to an embodiment of the present disclosure, the method includes: culturing the aforementioned recombinant cell or recombinant microorganism under conditions suitable for expressing the chimeric DNA polymerase, so as to obtain the chimeric DNA polymerase. Thus, the method according to the method of the embodiment of the present disclosure can obtain the chimeric DNA polymerases having the properties such as high processivity, high elongation rate, thermal stability, strong resistance to salts, and high fidelity, which can meet the requirements of DNA amplification, synthesis, detection, sequencing, etc., thereby having a broad application prospect.

Those skilled in the art can understand that the method for obtaining the chimeric DNA polymerase has the similar features and advantages of the chimeric DNA polymerases as described above, which will not be repeated herein.

Kit

In yet another aspect of the present disclosure, the present disclosure provides a kit. According to an embodiment of the present disclosure, the kit contains the aforementioned chimeric DNA polymerase, isolated nucleic acid, construct, recombinant cell or recombinant microorganism. Therefore, DNA amplification using the kit according to the embodiment of the present disclosure has the advantages such as high amplification product yield and high amplification accuracy, and thus the kit is suitable for wide production and application.

It should be noted that the kit of the present disclosure may further contain other reagents commonly used in the art, for example, buffers, primers, nucleoside triphosphates, etc., which can be flexibly selected according to the actual situation and are not specifically limited in the present disclosure.

It will be understood by those skilled in the art that the kit has the similar features and advantages of the chimeric DNA polymerases, the isolated nucleic acid, the construct, and the recombinant cell or recombinant microorganism, as described above, which will not be repeated herein.

Use

In yet another aspect of the present disclosure, the present disclosure provides use of the aforementioned chimeric DNA polymerase, the isolated nucleic acid, the construct, the recombinant cell or recombinant microorganism, or the kit in DNA amplification. As a result, the DNA amplification has the advantages of a high amplification product yield and high amplification accuracy, and is suitable for wide production and application.

According to embodiments of the present disclosure, the chimeric DNA polymerase, the isolated nucleic acid, the construct, the recombinant cell or recombinant microorganism, or the kit can be used for genetic screening, sequencing or mutation detection. The above DNA polymerases, due to their properties such as high processivity, high elongation rate, thermal stability, strong resistance to salts, and high fidelity, can be effectively applied to gene screening, sequencing, or mutation detection, which has high requirements for the amplification yield and fidelity.

It will be understood by those skilled in the art that that the use has the similar features and advantages of the chimeric DNA polymerases, the isolated nucleic acid, the construct, the recombinant cell or recombinant microorganism, or the kit, as described above, which will not be repeated herein.

The solutions of the present disclosure will be explained below in conjunction with the examples. Those skilled in the art will understand that the following examples are only used to illustrate the present disclosure, and should not be construed as limiting the scope of the present disclosure. The specific technique or condition in the examples are those described in the literatures in the related field or the product specification, unless they are specifically indicated. The reagents or instruments without indicating the manufacturers are conventional products that can be obtained from the market.

Example 1

Design and Construction of Chimeric DNA Polymerases

The Pfu, Pab, and KOD DNA polymerases have different phenotypic characteristics. Specifically, among all the DNA polymerases having thermal stability and fidelity, the Pfu DNA polymerase has the lowest error probability, with an error probability of about $2.0 \times 10^{-6}$. The Pab DNA polymerase also exhibits a low amplification probability and higher thermal stability. The KOD DNA polymerase, as a DNA polymerase with high amplification ability, has an amplification speed that is 2 times that of the Taq DNA polymerase and 6 times that of the Pfu DNA polymerase, and thus has a high amplification yield (about 300 nts).

The chimeric DNA polymerase in this example is a chimeric combination of the Pfu, Pab and KOD DNA polymerases (shown in FIG. 1). Specifically, nucleotide sequences (sites 1 to 390 and sites 1012 to 1119) in the N-end domain of the KOD DNA polymerase, a nucleotide sequence (sites 1771 to 2325) in the thumb domain of the KOD DNA polymerase, a nucleotide sequence (sites 391 to 1011) in the exonucleolytic domain of the Pab DNA polymerase, a sequence (sites 1345 to 1500) in the finger domain of the Pab DNA polymerase, and nucleotide sequences (sites 1120 to 1344 and sites 1501 to 1773) in the palm domain of the Pfu DNA polymerase were constructed between the XhoI/BamHI digestion sites of the prokaryotic expression vector pET28a. The vector carrying the above nucleotide sequences was transferred into *Escherichia coli* BL21 (DE3), followed by culturing to obtain the expression strains. The chimeric DNA polymerase exhibits high amplification capacity similar to the KOD DNA polymerase, and has a lower amplification mismatch probability than the KOD DNA polymerase.

Example 2

Fermentative Expression and Purification of Chimeric DNA Polymerase

1. Fermentation expression: the expression strains obtained in Example 1 were scaled up at a ratio of 1:100 and inoculated into a liquid LB medium containing kanamycin. The culture was shaken at 220 rpm and 37° ° C. until OD600=0.6, followed by adding 0.5 mM IPTG, and low temperature induction expression at 16° C. with shaking at 220 rpm overnight (16 h). The bacterial pellet was collected after centrifugation at 6000 rpm for 8 min.

2. Fermentation cell treatment: the bacteria were re-suspended with a bacteria re-suspending solution A (20 mM Tris, 300 mM NaCl, 20 mM Imidazole, 5% Glycerol, pH 8.0), at a mass-volume ratio of bacteria weight (g) to bacteria re-suspending solution (ml) being 1:20, followed by ultra-sonication. The supernatant was collected after a centrifugation at 12,000 rpm for 20 min. After denaturation in a water bath at 75° C. for 30 min, the supernatant was collected after a centrifugation at 12,000 rpm for 20 min.

3. Ni column purification: the collected supernatant was filtered through a 0.22 μm filtering device. After the Ni column was washed and equilibrated with the bacteria re-suspending solution A, the above filtrate through the 0.22 μm filter was added to the column, and the column was gradient-eluted with adjusting a concentration of imidazole in the eluent (20 mM Tris, 300 mM NaCl, 5% Glycerol, 500 mM Imidazole, pH 8.0). The fractions from the column were collected, and the active fractions were analyzed by SDS-PAGE. The fractions of pure target proteins observed on a Coomassie-stained SDS-PAGE gel were pooled.

Figure 2:
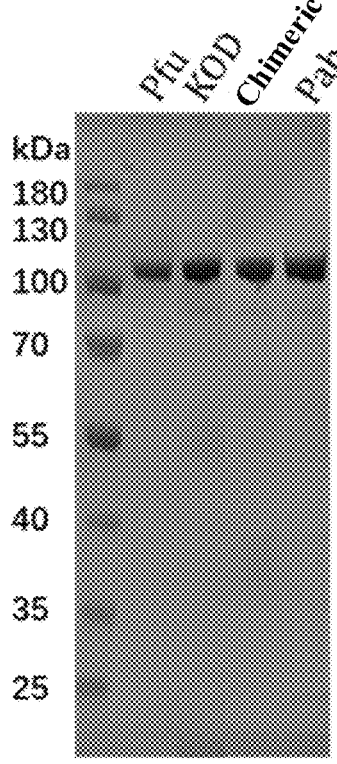
FIG. 2 is an electropherogram of enzyme expression and purification according to an embodiment of the present disclosure.

4. Anion column purification: the pooling sample of the above fractions was purified through an ion column to control endonuclease residues and nucleic acid residues in the sample. The pooling sample of fractions was dialyzed into Buffer C (20 mM Tris, 100 mM NaCl, 5% Glycerol, pH 8.0), the concentration of salt ions in Buffer D (20 mM Tris, 500 mM NaCl, 5% Glycerol, pH 8.0) was adjusted for gradient elution, and the collected elution column fraction was the novel chimeric DNA polymerase. The obtained sample was dialyzed to a storage system (20 mM Tris, 200 mM KCl, 50% Glycerol, 0.2 mM EDTA, 2 mM DTT, 0.001% Tween 20, 0.001% NP40, pH 8.0). The enzymes obtained from purification are illustrated in FIG. 2, and the target proteins with higher purity were obtained.

Example 3: Amplification Performance of Chimeric DNA Polymerase

The chimeric DNA polymerases obtained in Example 2 of the present disclosure were amplified with λDNA as a template, and the amplified fragments have a length of 2 Kb to 8 Kb. Among them, the extension time of the Pfu DNA polymerase was 60 s/kb, and the extension time of the Pab, KOD and chimeric DNA polymerase was 30 s/kb.

The primer sequences are as follows:

```
1am-F:
                                         (SEQ ID NO: 9)
CCTCTGTCGTTTCCTTTCTCTGTTTTTGTCCGTGG

1am2K-R:
                                        (SEQ ID NO: 10)
CGTCTGTTCATCGTCGTGGCGGCCCATAATAATCT

1am4K-R:
                                        (SEQ ID NO: 11)
GCACTCTTTCTCGTAGGTACTCAGTCCGGCTTCT

1am8K-R:
                                        (SEQ ID NO: 12)
CGGGAATACGACGGTTACCCACCACAAGCACG
```

Figure 3:
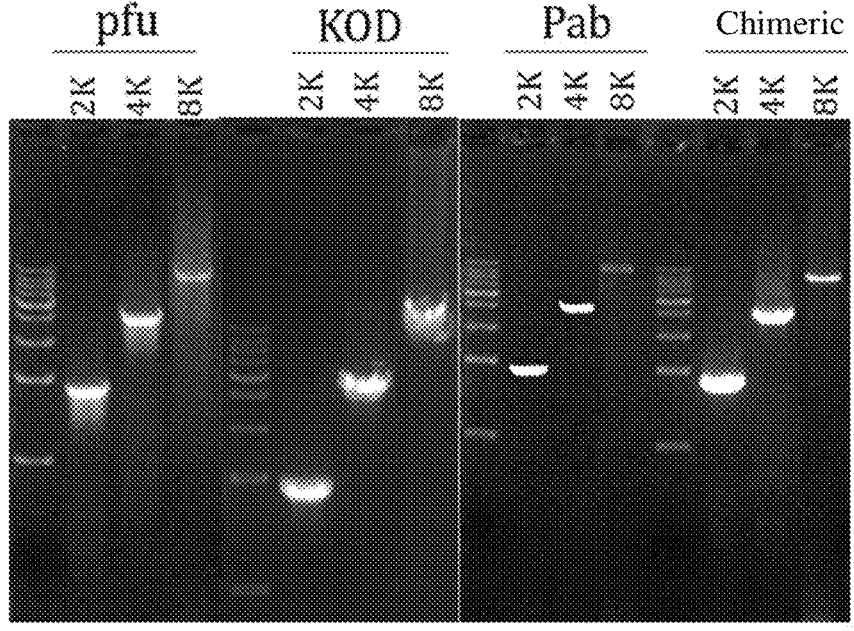
FIG. 3 is a comparison electropherogram of amplification performances of fragments with different amplification lengths according to an embodiment of the present disclosure.

The amplification reaction procedure and system are shown in Table 2. The results are illustrated in FIG. 3. FIG. 3 indicates that the new chimeric DNA polymerase has a higher yield of the amplified target product and better amplification effect than the Pfu and Pab DNA polymerase; and that the amplification effect of the chimeric DNA polymerases was comparable with the amplification effect of the KOD DNA polymerase.

TABLE 2

| Amplification reaction conditions | | | | |
|---|---|---|---|---|
| Temper-ature | Time | Number of cycles | Components | Volume (μl) |
| 94° C. | 3 min | 1 | 5× PCR Buffer | 5 |
| 95° C. | 20 sec | 30 | λDNA (10 ng/ul) | 1 |
| 60° C. | 15 sec | | Primer (10 uM) | 0.5 each |
| 72° C. | | | dNTPs (10 mM) | 0.4 |
| 72° C. | 5 min | 1 | Enzyme | 1 |
| 8° C. | ∞ | 1 | H₂O | Supplement to 25 μl |

Example 4

Amplification Fidelity Analysis of Chimeric DNA Polymerases

LacIQZ a gene was amplified respectively with the Pab DNA polymerase, the Pfu DNA polymerase, the KOD DNA polymerase, and the chimeric DNA polymerase. The amplified fragments and the vectors were digested with XbaI/NcoI double enzymes. The amplified fragments and the vector fragments were respectively collected with gel and enzymatically ligated, and the ligation mixture was transformed into E. coli DH5a and the cells were inoculated on LB-Amp-X-gal plates for culture. The number of blue bacterial colonies, the number of white bacterial colonies and the total number of bacterial colonies were counted, to calculate the fidelity.

The sequences of the primers for amplification of the LacIQZ a gene are as follows:

```
Lac-F:
                                        (SEQ ID NO: 13)
GTTTTCCCAGTCACGAC

Lac-R:
                                        (SEQ ID NO: 14)
GGTATCTTTATAGTCCTGTCG
```

Equation for calculating fidelity:

Mismatch ratio =

$$1 - \text{number of bases} \times \text{number of cycles}\sqrt{\dfrac{\text{number of blue bacterial colonies}}{\text{total number of bacterial colonies}}}$$

The results are shown in Table 3 below. The above results demonstrate that the chimeric DNA polymerase has improved amplification fidelity performance compared to the KOD DNA polymerase.

TABLE 3

| | Colony count and mismatch ratio | | | |
|---|---|---|---|---|
| | Number of white bacterial colonies | Number of blue bacterial colonies | Total number of bacterial colonies | Mismatch ratio ($\times 10^{-6}$) |
| Pfu | 183 | 9290 | 9473 | 1.41 |
| Kod | 472 | 7319 | 7791 | 4.51 |
| Pab | 157 | 8763 | 8920 | 1.28 |
| Chimeric DNA polymerase | 151 | 8105 | 8256 | 1.33 |

Example 5

Thermal Stability Assay of Chimeric DNA Polymerase

The Pab, Pfu, KOD and chimeric polymerases were each incubated at 98° C. for 0, 30, 60, 90, 120 or 180 minutes. After the incubation, *E. coli* gDNA was amplified with each of the above polymerases, and the PCR products were analyzed by agarose gel.

The amplification primer sequences:

```
Ecoli-F:
                               (SEQ ID NO: 15)
AGAGTTTGATCMTGGCTCAG Ecoli-R:
                               (SEQ ID NO: 16)
CGGTTACCTTGTTACGACTT
```

Figure 4:
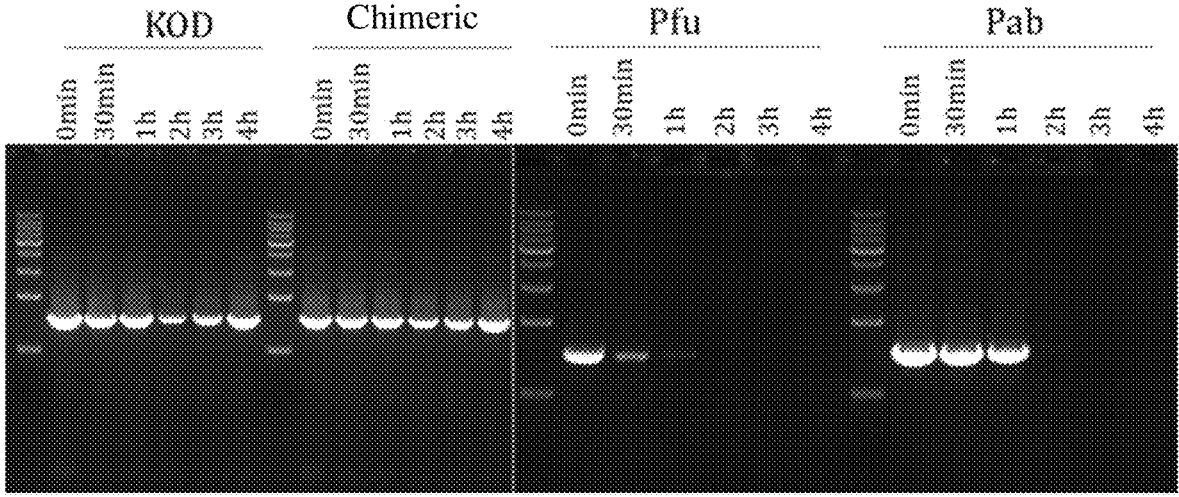
FIG. 4 is an electropherogram of thermal stability comparison according to an embodiment of the present disclosure.

The amplification system and amplification procedure can refer to Example 3. The results are shown in FIG. 4.

The results showed that no amplified fragments were observed by the Pfu DNA polymerase after 2 h of pre-incubation at 98° C.; no amplified fragments were observed by the Pab DNA polymerase after 3 h of pre-incubation at 98° C.; and the PCR product was obtained through amplification by the chimeric DNA polymerase at all test time points.

Example 6

Figure 5:
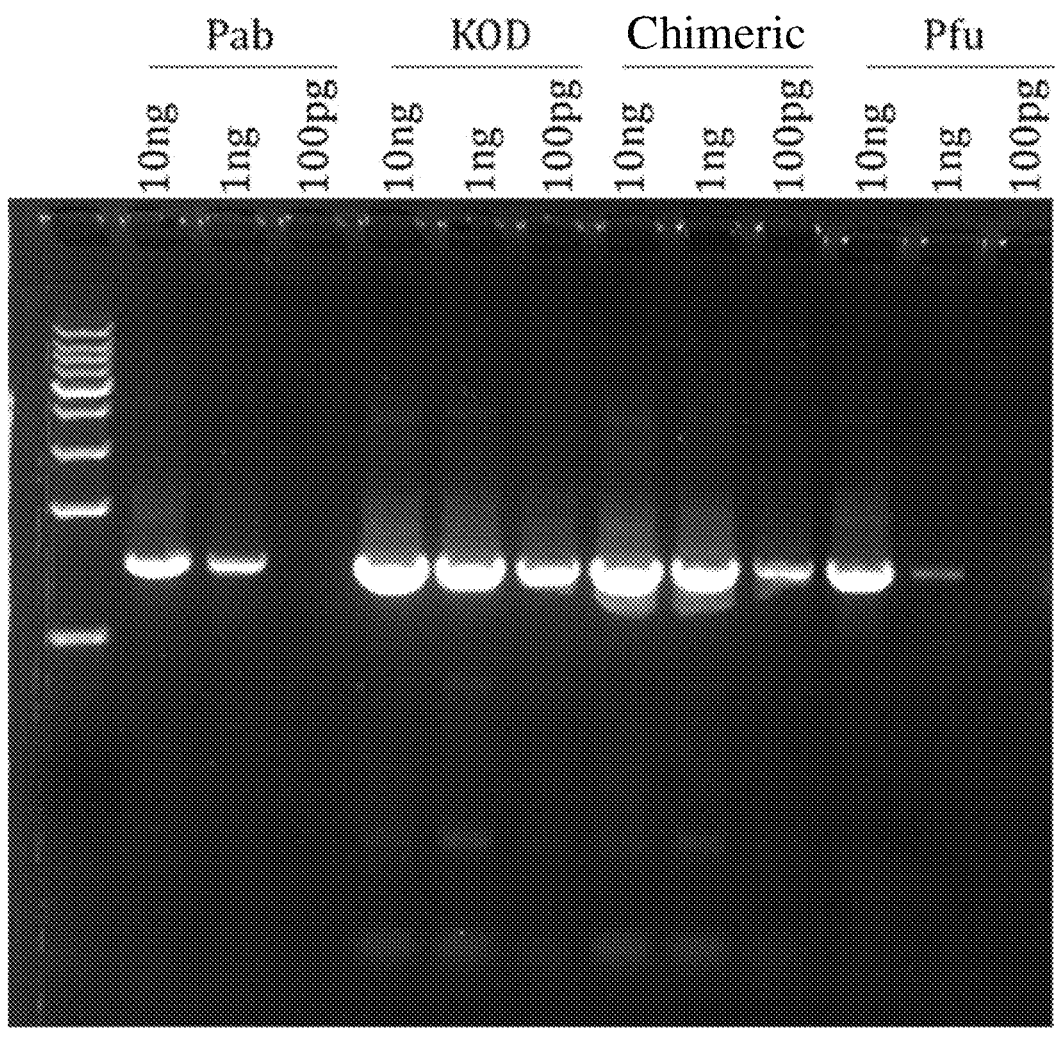
FIG. 5 is a comparison electropherogram of amplifications with different templates according to an embodiment of the present disclosure.

Amplification Using Chimeric DNA Polymerases Under the Condition of a Small Amount of Template 10 ng, 1 ng and 100 pg of *E. coli* gDNA were respectively added to the amplification system, and amplified with the Pfu, Pab, KOD and chimeric polymerases. The PCR products were analyzed by agarose gel. The amplification system and amplification procedure can refer to Example 3, and the sequences of the amplification primers can refer to Example 5. The results are shown in FIG. 5. With the three respective amounts of the added template, the target product can be obtained with a better yield through the amplification with the chimeric DNA polymerases.

In the specification, description with reference to the terms "an embodiment," "some embodiments," "example," "specific example," or "some examples", etc., mean that specific features, structures, materials or characteristics described in connection with the embodiment or example are included in at least an embodiment or example of the present disclosure. In this specification, schematic representations of the above terms are not necessarily directed to the same embodiment or example. Furthermore, the particular features, structures, materials or characteristics described may be combined in any suitable manner in any one or more embodiments or examples. Furthermore, those skilled in the art may combine the different embodiments or examples as well as the features of the different embodiments or examples described in this specification, without conflicting each other.

Although the embodiments of the present disclosure have been illustrated and described above, it should be understood that the above embodiments are exemplary and should not be construed as limiting the present disclosure. Those skilled in the art can make changes, modifications, substitutions and variations to the embodiments within the scope of the present disclosure.

What is claimed is:

1. A chimeric DNA polymerase, comprising:
a first peptide fragment comprising an amino acid sequence of sites 1 to 130 of a KOD DNA polymerase;
a second peptide fragment comprising an amino acid sequence of sites 131 to 337 of a Pab DNA polymerase, an N-terminal end of the second peptide fragment being connected to a C-terminal end of the first peptide fragment;
a third peptide fragment comprising an amino acid sequence of sites 338 to 373 of the KOD DNA polymerase, an N-terminal end of the third peptide fragment being connected to a C-terminal end of the second peptide fragment;
a fourth peptide fragment comprising an amino acid sequence of sites 374 to 448 of a Pfu DNA polymerase, an N-terminal end of the fourth peptide fragment being connected to a C-terminal end of the third peptide fragment;
a fifth peptide fragment comprising an amino acid sequence of sites 449 to 500 of the Pab DNA polymerase, an N-terminal end of the fifth peptide fragment being connected to a C-terminal end of the fourth peptide fragment;
a sixth peptide fragment comprising an amino acid sequence of sites 501 to 591 of the Pfu DNA polymerase, an N-terminal end of the sixth peptide fragment being connected to a C-terminal end of the fifth peptide fragment; and
a seventh peptide fragment comprising an amino acid sequence of sites 591 to 774 of the KOD DNA polymerase, an N-terminal end of the seventh peptide fragment being connected to a C-terminal end of the sixth peptide fragment.

2. The chimeric DNA polymerase according to claim 1, wherein the chimeric DNA polymerase has an amino acid sequence set forth as SEQ ID NO: 1.

3. An isolated nucleic acid, encoding the chimeric DNA polymerase according to claim 1.

4. The isolated nucleic acid according to claim 3, wherein the isolated nucleic acid has a nucleotide sequence set forth as SEQ ID NO: 2.

5. A construct, comprising the isolated nucleic acid according to claim 3.

6. A recombinant cell or recombinant microorganism, containing the isolated nucleic acid according to claim 3.

7. A method for obtaining the chimeric DNA polymerase according to claim 1, comprising:
culturing a recombinant cell or recombinant microorganism containing an isolated nucleic acid encoding the chimeric DNA polymerase under conditions suitable for expressing the chimeric DNA polymerase to obtain the chimeric DNA polymerase.

8. A kit, containing the chimeric DNA polymerase according to claim 1.

9. The chimeric DNA polymerase according to claim 1, wherein the chimeric DNA polymerase is used in DNA amplification, genetic screening, sequencing, or mutation detection.

10. The isolated nucleic acid according to claim 3, wherein the isolated nucleic acid is used in DNA amplification, genetic screening, sequencing, or mutation detection.

11. The construct according to claim 5, wherein the construct is used in DNA amplification, genetic screening, sequencing, or mutation detection.

12. The recombinant cell or recombinant microorganism according to claim 6, wherein the recombinant cell or recombinant microorganism is used in DNA amplification, genetic screening, sequencing, or mutation detection.

13. The kit according to claim 8, wherein the kit is used in DNA amplification, genetic screening, sequencing, or mutation detection.

* * * * *